US006232095B1

(12) United States Patent
Kmiec et al.

(10) Patent No.: US 6,232,095 B1
(45) Date of Patent: *May 15, 2001

(54) RECOMBINANT HELIX MODIFICATION RECOGNITION PROTEINS AND USES THEREOF

(75) Inventors: Eric B. Kmiec, Malvern, PA (US); William K. Holloman, Yorktown Heights, NY (US); David Gerhold, Lansdale, PA (US)

(73) Assignee: Thomas Jefferson University, Philadelphia, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/563,524

(22) Filed: Nov. 28, 1995

(51) Int. Cl.⁷ .......................... C12N 15/00; C12N 15/63; C12N 1/20; C12N 15/85; C07H 21/04; C07K 14/00

(52) U.S. Cl. ................... 435/69.1; 435/320.1; 435/325; 435/69.7; 435/252.3; 536/23.4; 536/23.74; 530/350; 530/371

(58) Field of Search ...................... 435/6, 252.3, 69.1, 435/69.7, 325, 320.1; 530/350, 371, 387.1; 536/23.1, 23.4, 23.74; 424/130.1

(56) References Cited

U.S. PATENT DOCUMENTS 5,459,039  10/1995  Modrich et al. ...................... 435/6

OTHER PUBLICATIONS

Lewin. Science 237: 1570 (1987).*
Fitch et al. P.N.A.S. 80: 1382–1386 (1983.*
George et al. Macromolecular Sequencing & Synthesis Selected Methods and Applications, 1988, D.H. Schlesinger (ed.) Alan R. Liss, Inc., New York, N.Y. pp. 127–149.*
Beeck et al. Cell 50: 667 (1987).*
Alani et al., Genes & Develop. 9:234–247, 1995.
Bhattacharyya and Lilley, Nucl. Acids. Res. 17:6821–6840, 1989.
Bianchi et al., EMBO J. 11:1055–1063, 1992.
Bruhn et al., PNAS USA 89:2307–11, 1992.
Chi and Kolodner, J. Biol. Chem. 269:29984–29992, 1994.
Cotton, Current Opinion in Biotech. 3:24–30, 1992.
Drlica and Rouviere–Yaniv, Microbiol. Rev. 51:301–319, 1987.
Gerhold et al., Nucleic Acids Research 22:3773–3778, 1994.
Goodwin et al., Eur. J. Biochem. 38:14–19, 1973.
Grosschedl et al., Trends Genet. 10:94–100, 1994.
Holloman, Nucleic Acids and Mol. Biol. 2:198–205, 1988.
Johns, in The HMG Chromosomal Proteins (Johns, E.W. ed.) pp. 1–7, Academic Press, 1982.
Kotani et al., Chromosoma 102:348–354, 1993.
Laudet et al., Nucleic Acids Res. 21:2493–2501, 1993.
Lee et al., Cell 81:1013–1020, 1995.
Parker et al., PNAS USA 89:1730–1734, 1992.
Pil et al., PNAS USA 90:9465–9469, 1993.
Pontiggia et al., Mol. Microbiol. 7:343–350, 1993.
Short et al., Nucleic Acids Res. 16:7583–7600, 1988.
Thiyagarajan et al., Biochim. Biophys. Acta 1173:155–164, 1993.
Wang et al., J. Biol. Chem. 268:17571–17577, 1993.
Weir et al., EMBO J. 12:1311–1317, 1993.
Werner et al., Cell 81:705–714, 1995.
Yang and Nash, Cell 57:869–880, 1989.

* cited by examiner

Primary Examiner—Lisa B. Arthur
(74) Attorney, Agent, or Firm—Reed Smith Shaw & McClay LLP

(57) ABSTRACT

Disclosed are the Hmp class of polypeptides, DNA sequences encoding those polypeptides, and uses thereof, particularly in methods and kits for mismatch (for example, mutation) detection.

43 Claims, 22 Drawing Sheets

```
  1  CAACCTCATCAAACACTAATTCACAATGTCTGAGCCCTCCAAGGTTAACGGGTATGTTTC   60
                              M  S  E  P  S  K  V  N  G

61  TCGTCACCACACAACATGTTGATCTCTGCGCTGCCGTCAAACAGCTTTCTAACCACTGCA  120

121  CCCTCTGCTCTATCCGCACACAGAAACTACAACTCGGTCGCTGGTACCGTCAAGGAGACC  180
                             N  Y  N  S  V  A  G  T  V  K  E  T

181  ATCGGCAACGCTCTCGGCTCCACTGAGTGGCAAAAGGCTGGCAAGGAGCAGCACGCCAAG  240
      I  G  N  A  L  G  S  T  E  W  Q  K  A  G  K  E  Q  H  A  K

241  GGCGAGGGCGAGATCAAGGCTGCTCAGGCCCAGGGCTACGCCGAGGGCACTAAGGACCAG  300
      G  E  G  E  I  K  A  A  Q  A  Q  G  Y  A  E  G  T  K  D  Q

301  GTCTCGGGTAAGATCGACAACGTTGTCGGCGCTGTCACCGGTGACAAGTCCAAGGAACTG  360
      V  S  G  K  I  D  N  V  V  G  A  V  T  G  D  K  S  K  E  L

361  TCCGGCAAGGCTCAGCAGGAGTCTGGCAAGGCTCAGAAGGAGATCAACTCCTAAACGGTT  420
      S  G  K  A  Q  Q  E  S  G  K  A  Q  K  E  I  N  S

421  ATTTGTTCGAATTGATTTGATAGATCATCAGTCAATCAGCTCTCTACCTTACGCTTAATC  480

481  GTACAACGTAGGCATGCCAATGAATATACCAATCCAGANTGTCACAATTCTCATGTTAAA  540

541  AAAAAAAAAAAAAAA  555
```

Figure 2

```
Hmp1    1 MSEPSKVNGN.....YNSV......AGTVKETIGNALGSTEWQKAGKEQHAKG..EGEIKAAQ  50
          |       |    | ||       | |||  | ||    |  |  |         |
RecA  204 FGNPETTTGGNALKFYASVRLDIRRIGAVKEG.ENVVGSETRVKVVKNKIAAPFKQAEFQILY 265

Hmp1   51 AQG...YAEGTKDQVSGKIDNVVGAVTGDKSKELS.GKAQ.....QESGKAQKEINS  98
          |  |  |    | |      ||   |      |||              |||
RecA  266 GEGINFYGELVDLGVKEKLIEKAGAWYSYKGEKIGQGKANATAWLKDNPETAKEIEK 322
```

Figure 22

RECOMBINANT HELIX MODIFICATION RECOGNITION PROTEINS AND USES THEREOF

BACKGROUND OF THE INVENTION

This invention relates to proteins that bind nucleotide mismatches, DNAs encoding such proteins, and uses thereof, particularly in mismatch detection assays.

Mutation detection techniques provide powerful tools for the prediction and diagnosis of disease arising from one or more changes in a nucleotide sequence. Such changes generally occur in coding regions and result in protein products that are either inactive or are altered in their level or type of activity. Less commonly, mutations resulting in disease states occur in nucleotide sequences that do not encode a protein product; for example, mutations in repetitive DNA have been shown to be associated with such diseases as human fragile-X syndrome, spinal and bulbar muscular dystrophy, and myotonic dystrophy.

To detect mismatches at the nucleic acid level, a number of screens have been developed, many employing a technique commonly referred to as heteroduplex analysis. This technique involves the formation of a duplex between one strand of a control nucleic acid (typically, of wild-type sequence) and one strand of a test nucleic acid (for example, one suspected of including a mutation). The presence of a mismatch in the duplex is then revealed by any of a number of standard approaches, including RNAse A digestion, chemical cleavage, or PCR-based or primer extension-based techniques (reviewed in Cotton, Curr. Opinion in Biotech. 3: 24, 1992).

Another means by which mismatches may be identified in a heteroduplex molecule is by the use of mismatch-specific proteins. These proteins are capable of recognizing and either binding or cleaving at or near a site of mismatch. One particular class of mismatch-specific binding proteins is the "Mut" series of bacterial polypeptides. An exemplary member of this class, the MutS protein, has been reported to bind heteroduplex DNA at sites of certain base pair mismatches and at loops resulting from deletions or insertions of up to four bases in length (Parker et al., Proc. Natl. Acad. Sci. USA 89: 1730–1734, 1992; Modrich et al., U.S. Pat. No. 5,459,039, 1995).

Given the role played by mismatch-specific proteins in mutation detection assays, the isolation and characterization of additional proteins having the capacity to identify mutant sites in nucleic acid substrates is of great value. These proteins find use in assays for the diagnosis and prognosis of diseases such as cancer, and are also useful for perinatal screening for inherited diseases, differential diagnosis of diseases not readily detectable by conventional tests (for example, Marfan's syndrome), and the detection of genetic alleles (for example, for genetic mapping, tissue matching, or identification purposes).

SUMMARY OF THE INVENTION

In general, the invention features a substantially pure recombinant Hmp polypeptide. Preferably, this polypeptide includes an amino acid sequence substantially identical to the sequence shown in FIG. 2 (SEQ ID NO: 2), for example, includes the exact amino acid sequence shown in FIG. 2 (SEQ ID NO: 2); is derived from a fungus (for example, Ustilago); or is fused to a second polypeptide (for example, bacteriophage T4 endonuclease VII).

In a related aspect, the invention also features substantially pure DNA that includes a sequence encoding a recombinant Hmp polypeptide. Preferably, this DNA encodes an amino acid sequence substantially identical to the amino acid sequence shown in FIG. 2 (SEQ ID NO: 2); includes a DNA sequence substantially identical to the DNA sequence shown in FIG. 2 (SEQ ID NO: 3); or includes the exact DNA sequence shown in FIG. 2 (SEQ ID NO: 3).

In other related aspects, the invention features substantially pure DNA that includes a sequence encoding an Hmp fusion polypeptide; vectors and cells that include any of the substantially pure DNAs of the invention; substantially pure antibody that specifically binds an Hmp polypeptide (for example, an Hmp1 polypeptide); and a method of producing a recombinant Hmp polypeptide that involves providing a cell transformed with DNA encoding an Hmp polypeptide positioned for expression in the cell, culturing the transformed cell under conditions for expressing the DNA, and isolating the recombinant Hmp polypeptide (for example, the recombinant Hmp1 polypeptide). Also included in the invention is an Hmp polypeptide produced by expression of the substantially pure DNAs of the invention.

In yet another related aspect, the invention features a kit for the detection of a mismatch in a test nucleic acid sequence that includes a substantially pure Hmp polypeptide. In preferred embodiments, the Hmp polypeptide is purified from Ustilago maydis; the Hmp polypeptide is recombinant; the Hmp polypeptide is an Hmp1 polypeptide; the Hmp1 polypeptide is purified from Ustilago maydis; the Hmp1 polypeptide is recombinant; and the Hmp polypeptide is fused to a second polypeptide.

In a final related aspect, the invention features a method for detecting at least one mismatch in a test nucleic acid which hybridizes to a control nucleic acid, the method involving: a) providing a single-stranded control nucleic acid; b) annealing the single-stranded control nucleic acid to a single-stranded test nucleic acid to form a hybridized duplex between the nucleic acids; c) contacting the duplex with an Hmp polypeptide capable of recognizing at least one base pair mismatch in the duplex, under conditions allowing the Hmp polypeptide to bind the duplex at or near the site of mismatch; and d) detecting the binding as an indication of the presence of at least one mismatch in the test nucleic acid.

In preferred embodiments, the mismatch is a mutation; either or both of the test nucleic acid and the control nucleic acid is amplified; the Hmp polypeptide is derived from a eukaryotic organism; the Hmp polypeptide is purified from Ustilago maydis; the Hmp polypeptide is recombinant; the Hmp polypeptide is an Hmp1 polypeptide; the Hmp1 polypeptide is purified from Ustilago maydis; the Hmp1 polypeptide is recombinant; and the Hmp polypeptide is fused to a second polypeptide.

By "Hmp" is meant any polypeptide within the class of helix modification recognition proteins. Such polypeptides are capable of binding cruciform DNA, DNA duplexes exhibiting one or more mismatched base pairs (for example, substitutions, insertions, or deletions), or otherwise distorted helical DNA. In particular, an Hmp polypeptide is capable of binding, under standard solution conditions, to a sequence that includes a C/C mismatch, in preference to binding an otherwise identical sequence lacking a mismatch. Hmp polypeptides are further characterized by their capacity to bind all possible base pair mismatches (i.e., A/A, T/T, C/C, G/G, A/C, A/G, C/T, and T/G mismatches), and to do so in preference to binding homoduplex DNA (i.e., DNA lacking mismatched nucleotides). By "HMP" is meant a gene encoding a member of the Hmp class of polypeptides (as defined above).

By "Hmp1" is meant one member of the Hmp class of polypeptides having the amino acid sequence shown in FIG. 2 (SEQ ID NO: 2) or a sequence that is substantially identical to that amino acid sequence. An Hmp1 polypeptide is encoded by an "HMP1" nucleic acid sequence.

By "polypeptide" or "protein" is meant any chain of amino acids, regardless of length or post-translational modification (e.g., glycosylation or phosphorylation).

By "substantially identical" is meant a polypeptide exhibiting at least 60%, preferably 75%, more preferably 90%, and most preferably 95% identity to a reference amino acid sequence or is meant a nucleic acid sequence exhibiting at least 50%, preferably 70%, more preferably 85%, and most preferably 90% identity to a reference nucleic acid sequence. For polypeptides, the length of comparison sequences will generally be at least 16 amino acids, preferably at least 20 amino acids, more preferably at least 25 amino acids, and most preferably 35 amino acids. For nucleic acids, the length of comparison sequences will generally be at least 30 nucleotides, preferably at least 60 nucleotides, more preferably at least 75 nucleotides, and most preferably 110 nucleotides.

Sequence identity is typically measured using sequence analysis software (e.g., the Sequence Analysis Software Package of the Genetics Computer Group, University of Wisconsin Biotechnology Center, 1710 University Avenue, Madison, Wis. 53705). Such software matches similar sequences by assigning degrees of homology to various substitutions, deletions, insertions, and other modifications.

By a "substantially pure polypeptide" is meant a polypeptide which has been separated from those components which naturally accompany it. Typically, the polypeptide is substantially pure when it is at least 60%, by weight, free from the proteins and organic molecules with which it is naturally associated. Preferably, the preparation is at least 75%, more preferably at least 90%, and most preferably at least 99%, by weight, the desired polypeptide. A substantially pure polypeptide may be obtained, for example, by extraction from a natural source (e.g., *Ustilago maydis*); by expression of a recombinant nucleic acid encoding the polypeptide in a cell in which it is naturally produced or in any other cell; by chemical protein synthesis; or by a combination of these or other standard techniques. Purity may be measured by any appropriate method, e.g., polyacrylamide gel electrophoresis or HPLC analysis.

By "substantially pure DNA" is meant DNA that is free of the genes which, in the naturally-occurring genome of the organism from which the DNA of the invention is derived, flank the gene. The term therefore includes, for example, a recombinant DNA which may be incorporated into a vector, an autonomously replicating plasmid, a phage, a virus, or into the genomic DNA of a prokaryote or eukaryote; or which exists as a separate molecule (e.g., a cDNA or a genomic or cDNA fragment produced by PCR or restriction endonuclease digestion) independent of other sequences. It also includes a recombinant DNA which is part of a hybrid gene encoding one or more additional amino acids.

By "transformed cell" is meant a cell into which (or into an ancestor of which) has been introduced, by means of recombinant DNA techniques, a DNA molecule encoding (as used herein) an Hmp polypeptide.

By "positioned for expression" is meant that a DNA molecule is positioned adjacent to a nucleotide sequence which directs transcription and translation of the sequence (i.e., facilitates the production of, e.g., an Hmp polypeptide or Hmp mRNA molecule).

By "promoter" is meant a minimal sequence that is sufficient to direct transcription. A promoter may also include those elements which are sufficient to render transcription controllable for cell-type specific, tissue-specific, or inducible expression; such elements may be located either 5' or 3' to a coding sequence or gene.

By "operably linked" is meant that a coding sequence or gene and regulatory sequence(s) are connected in such a way as to permit gene expression when the appropriate molecules (e.g., transcriptional activator proteins) are bound to the regulatory sequence(s).

By "substantially pure antibody" is meant antibody (including a polyclonal antibody preparation) which is at least 60%, by weight, free from proteins and other organic molecules with which it is naturally associated. Preferably, the preparation is at least 75%, more preferably 90%, and most preferably at least 99%, by weight, the antibody (or polyclonal antibody preparation) of interest. A substantially pure antibody may be obtained, for example, by affinity chromatography using a recombinantly-produced polypeptide or by using one or more conserved motif peptides recognized by the antibody, in conjunction with standard techniques.

By "specifically binds" is meant that an antibody recognizes and binds a polypeptide of interest, but which does not substantially recognize and bind other molecules in a sample, e.g., a biological sample, which naturally includes the polypeptide.

By "mutation" is meant any nucleotide sequence variation. As used herein, this term includes frequently encountered genetic variants (for example, genetic alleles) as well as sequence changes which are less frequently or infrequently observed. The term encompasses any nucleotide change (i.e., any single or multiple base pair substitution, deletion, or insertion).

By "duplex" is meant a structure formed between two annealed strands of nucleotides (e.g., one test nucleic acid strand and one control nucleic acid strand) in which sufficient sequence complementarity exists between the strands to maintain a stable hybridization complex. As used herein, a duplex may be formed between two annealed strands in which one or more nucleotides in the first strand do not or cannot appropriately base pair with one or more nucleotides in the second, opposing strand; this occurs, for example, when one strand is of wild-type sequence, and the second strand includes a base substitution (i.e., a bubble), or an insertion or deletion (i.e., a bulge), each of which has been disclosed in Bhattacharya and Lilley (*Nucl. Acids. Res.* 17: 6821–6840, 1989).

By "mismatch" is meant that a nucleotide in one strand does not or cannot pair through Watson-Crick base pairing and π-stacking interactions with a nucleotide in an opposing complementary strand. For example, adenine in one strand would form a mismatch with adenine in an opposing nucleotide strand. In addition, a mismatch occurs when a first nucleotide cannot pair with a second nucleotide in an opposing strand because the second nucleotide is absent (i.e., an unmatched nucleotide).

By "control nucleic acid" is meant any nucleotide sequence against which a "test nucleic acid" may be compared as a means of detecting a "mismatch" (as defined above) in the test sequence. A control nucleic acid and/or test nucleic acid of the invention may be composed of any strand of nucleotides, including modified or derivatized nucleotides (for example, inosine), and the nucleotides within the strand may be linked by any means, for example, by nucleic acid bonds or by peptide bonds (as is the case for peptide nucleic acids (PNAs)). Preferably, for a given mutation detection assay, the control and test nucleic acids are of approximately the same length, but this is not required so long as stable hybridization between the strands is possible. Although control and test nucleic acids of any length are encompassed by the invention, a preferred length for these sequences is 10,000 nucleotides or less, preferably, 1000 nucleotides or less (for example, 500–1000 nucleotides), more preferably, 500 nucleotides or less (for example, 200–500 nucleotides), and most preferably 200 nucleotides or less (for example, 35–200 nucleotides). Control and test nucleic acids may be derived from any source; for example, either or both may be obtained from a cell or other sample (for example, a biological sample), or may be generated by recombinant means, by amplification (for example, by PCR or LCR), by chemical synthesis, or by a combination of any of these standard techniques.

As described above, Hmp polypeptides may be used as probes for mismatch detection and, for this purpose, these polypeptides provide significant advantages over currently available mismatch detection techniques. Importantly, Hmp polypeptides recognize all possible mismatched base pairs under standard solution conditions, thereby maximizing the number and variety of different inherited and somatic mutations that may be detected in any given nucleotide sequence. In addition, this general ability to recognize any mismatched sequence facilitates mutation detection that requires little or no previous knowledge about either the identity of a sequence variation or its position on the chromosome or other test nucleic acid sequence. As a result of this ability to generally detect mismatched nucleotides, Hmp polypeptides provide advantages over many other detection techniques, such as allele-specific oligonucleotides, which only allow detection of known mutations at specific, previously determined sites. Hmp polypeptide-based detection techniques also provide improvements over direct DNA sequencing because they are less laborious and less expensive than sequencing, and, in addition, because they allow resolution of mutation sites even in heterozygotes, an analysis which often proves difficult using sequencing type methods.

Moreover, due to their small size, high stability, capacity to bind relatively tightly without the need for auxiliary proteins, and ability to bind mismatches (for example, C/C mismatches) in solution, Hmp polypeptides are unusually well suited to standard signal generation and detection assays. Hmp polypeptides, for example, may be used in any standard assay that involves antigen-antibody or nucleotide probe based techniques, and these polypeptides provide specific and selective mutation detection capabilities.

Finally, because Hmp polypeptides recognize and bind mismatch-containing heteroduplexes, even in the presence of homoduplex sequences and even when these homoduplexes are present in large excess, the present invention facilitates the detection of rare mutation events by "capture" of a mismatch-containing sequence. In one particular example, immobilized Hmp polypeptide may be used to perform the capture step (for example, on a column or filter), and the captured heteroduplex analyzed as an indication of the presence of a mutation. In addition, if desired, the captured nucleotide sequence may be amplified (for example, by PCR) to enhance signal output or to facilitate further investigation (for example, precise sequence determinations). Because Hmp polypeptides facilitate this type of mismatch detection under conditions where very small amounts of mismatched sequence are available for detection, these polypeptides provide important reagents for the identification of rare mutation events.

The many advantages afforded by Hmp polypeptides make them unusually useful probes for the detection of mutations associated with diseases such as cancer (for example, mutations in the p53, Rb-1, BRCA-1, BRCA-2, or p16 genes), or for detecting inherited diseases exhibiting high rates of spontaneous mutations (for example, Marfan Syndrome), or diseases that involve contributions from several different genes (as is the case, for example, for diabetes and cardiovascular disease).

Unless otherwise defined, all technical terms and scientific terms used herein have the same meaning as commonly understood by one of ordinary skill in the art to which this invention belongs. All publications mentioned herein are incorporated by reference.

Other features and advantages of the invention will be apparent from the following description of the preferred embodiments thereof, and from the claims.

BRIEF DESCRIPTION OF THE DRAWINGS

FIG. 1A illustrates the structure of cruciform DNA formed by annealing two partially complementary oligonucleotides of 61 bp (SEQ ID NOS: 9 and 10), each containing a unique internal self-complementary stretch of nucleotides.

FIG. 1B illustrates the structure of an open-ended duplex DNA molecule of 50 bp containing a single mismatched base pair, formed by annealing two complementary oligonucleotides (SEQ ID NOS: 12–19).

FIG. 1C illustrates the structure of a hairpin DNA duplex containing a single mismatched base pair, formed by annealing a self-complementary oligonucleotide (SEQ ID NOS: 20–22).

FIG. 2 is an illustration depicting the HMP1 genomic nucleotide sequence (SEQ ID NO: 1) and the predicted Hmp1 polypeptide amino acid sequence (SEQ ID NO: 2). The HMP1 nucleotide sequence was compiled from both cDNA and genomic fragments containing the HMP1 gene. The underlined segment of the nucleotide sequence shows both the nucleotide sequence and the position of the HMP1 intron. Nucleotides designated in bold show the initiation ("ATG") and termination ("TAA") codons, respectively. The translated amino acid sequence of the Hmpl polypeptide (SEQ ID NO: 2) is indicated beneath the corresponding open reading frame of the HMP1 gene (SEQ ID NO: 3).

FIG. 10A is a graph showing a competition assay for binding specificity to heteroduplex DNA containing a C/T mismatch. Reactions (20 μl) contained 15 nM $^{32}$P-labeled heteroduplex DNA (50-mer) with a C/T mismatch at position 25, 1.5 μM recombinant Hmp1 polypeptide, and the indicated concentrations of unlabeled DNAs added as competitors. After 30 minutes at 30° C., the reaction mixtures were passed through nitrocellulose filters, and the heteroduplex DNA retained was determined by scintillation counting. Competitor DNAs were as follows: homoduplex control (closed triangles); heteroduplex DNA with a C/T mismatch (closed circles); and cruciform DNA (closed squares).

FIG. 10B is a bar graph showing a competition assay for binding specificity to heteroduplex DNA (50-mer) containing a C/T mismatch. Reactions (20 μl) contained 15 nM $^{32}$P-labeled heteroduplex DNA (50-mer) with a C/T mismatch at position 25, 1.5 μM recombinant Hmp1 polypeptide, and the indicated unlabeled heteroduplex or cruciform DNA added to a final concentration of 75 nM as competitor. The bar graph indicates the relative ranking of the competitors for binding.

FIG. 22 is a schematic illustration showing the amino acid identity between the Hmp1 polypeptide and the C-terminus of the RecA protein. An alignment is shown between the Hmp1 polypeptide and a 119 residue segment at the carboxyl terminus of *E. coli* RecA protein (amino acids 204–322). *U. maydis* Hmp1 polypeptide is 30% identical (or 54% if conservative substitutions are included) over this segment of RecA protein. Sequences were aligned with the use of the Genetics Computer Group package software (gap penalty, 3.0; gap length penalty, 0.1). Vertical lines indicate amino acid identities.

DETAILED DESCRIPTION

Figure 1:
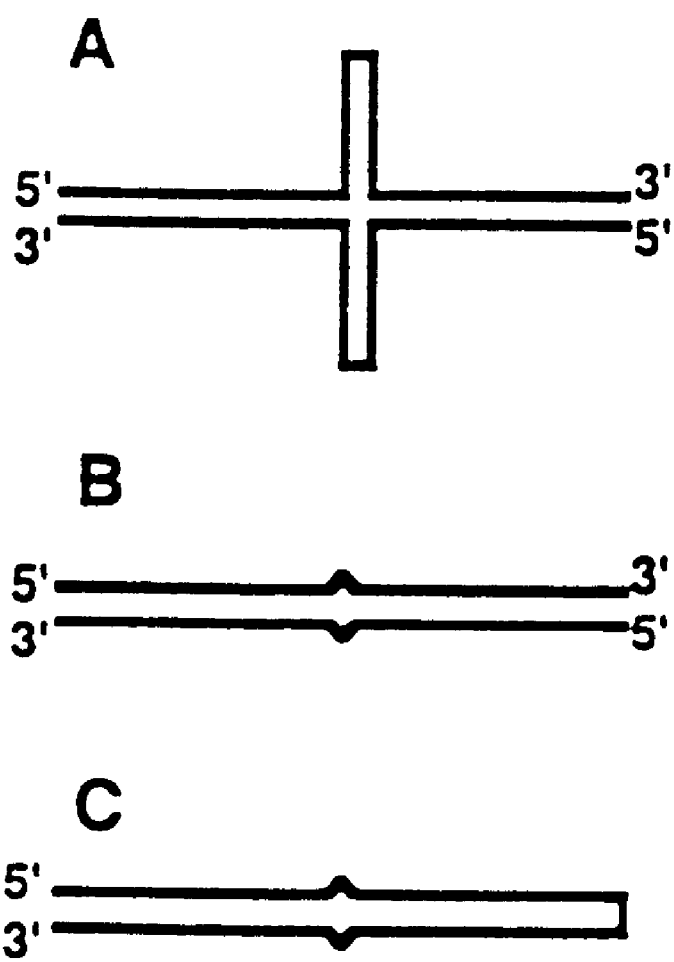
FIGS. 1A–C are a set of schematic illustrations showing the conformations of DNA binding substrates.

There now follows a description of the cloning and characterization of an HMP gene and the overexpression of an Hmp polypeptide of the invention. This example is provided for the purpose of illustrating the invention, and should not be construed as limiting.

Isolation of cDNA and Genomia DNA Encoding *Ustilago maydis* Hmp1 Polypeptide

A *Ustilago maydis* cDNA library was constructed by standard techniques and screened (also by standard techniques) using degenerate oligonucleotides derived from a partially-purified protein fraction having cruciform binding activity prepared from *Ustilago maydis* as follows.

Preparations of cruciform binding activity from acid extracts of crushed cells of Ustilago were obtained as described previously by Kotani et al. (*Chromosoma* 102:348–354, 1993). From these preparations, 220 pmoles of Hmp1 polypeptide was isolated, the polypeptide digested with trypsin, and the resulting peptides fractionated by high performance liquid chromatography (HPLC) according to standard methods. Two HPLC-purified peptides were then sequenced on an Applied Biosystems 477A sequencer with an on-line detector for phenylthiohydantoin-derivatized amino acids, and the following amino acid sequences obtained: AAAQAQGYAEGTKDQVSGKIDN (SEQ ID NO: 23) and ETIGNALGSTEWQK (SEQ ID NO: 4).

Oligonucleotides for use as polymerase chain reaction (PCR) primers were designed from the sequence of the 22 amino acid residue peptide (SEQ ID NO: 23) and used to amplify a fragment from genomic *Ustilago maydis* DNA. These primers were 5'ACGGATCCGCICAA/GGCICAA/GGGITA (SEQ ID NO: 5) and 5'CGGAATTCTTA/GTCIATT/CTTICCIITAIAC (SEQ ID NO: 6). To facilitate directional cloning, the primers included either a BamHI or EcoRI restriction enzyme site. In addition, as noted in the above primer sequences, each contained either a mixture of two nucleotides or inosine residues at wobble positions.

PCR amplification was performed in a standard reaction (50 μl) that contained 1.2 ng of *U. maydis* genomic DNA, 0.5 μM of each primer, 0.2 mM of each deoxynucleoside triphosphate, 2.5 mM MgCl$_2$, and 2.5 units of AmpliTaq DNA polymerase (Perkin-Elmer Cetus, Foster, Calif.). Annealing, elongation, and denaturation cycling conditions were 45 seconds at 38° C., 20 seconds at 74° C., and 2 minutes at 94° C., respectively. After 2 rounds of 40 cycles each, an ≈70 bp DNA fragment was visible after electrophoresis of the reaction mixture in a 1.5% agarose gel and ethidium bromide staining. The amplified fragment was isolated from the gel, digested with BamHI and EcoRI, and inserted into the corresponding sites of a pBluescript II SK$^+$ plasmid vector (Stratagene Cloning Systems, La Jolla, Calif.). The nucleotide sequence of the amplified 70 bp fragment was determined and found to encode a peptide corresponding to the sequence of the *U. maydis* peptide of SEQ ID NO: 23.

Radiolabeled probe was prepared from the 70 bp PCR-amplified fragment by random priming. This probe was then used to screen a *U. maydis* cDNA library prepared in λZAP II (Stratagene, La Jolla, Calif.) according to standard methods. The resulting recombinant plaques were lifted onto membrane filters (Dupont NEN, Boston, Mass.), and hybridization using the radiolabeled probe was performed following the manufacturer's protocol. Among the ≈10$^6$ plaques which were screened, approximately 250 were found to hybridize to the probe. Phagemids contained within the lambda vector were isolated after in vivo excision according to Short et al. (*Nucleic Acids Res.* 16: 7583–7600, 1988).

DNA sequence determination of the positive clones was carried out through automated sequencing using an Applied BioSystems 373 sequencer (Foster City, Calif.). Sequence analysis performed on phagemids corresponding to the 11 original isolates indicated that all contained inserts of ≈500 bp. The sequences were found to be essentially identical, except for two cases of differences at the site of polyA addition and one case where the 5' end was truncated by 65 residues.

Figure 3:
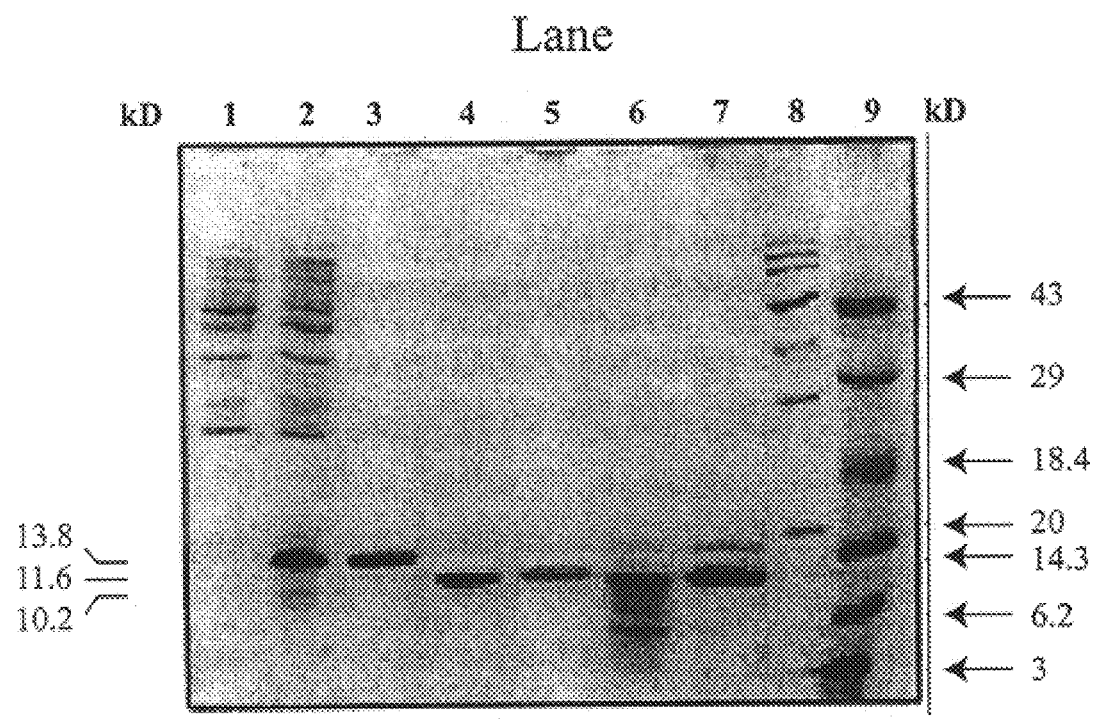
FIG. 3 is a photograph of an SDS-PAGE gel analysis of Hmp1 polypeptide. Samples containing approximately 1 µg of protein were analyzed by electrophoresis under denaturing conditions in a 15% polyacrylamide gel. After electrophoresis the gel was stained with Coomassie blue. Lane 1, crude extract from uninduced cells; lane 2, crude extract from IPTG-induced cells (1 hr post-induction); lane 3, histidine-leader Hmpl fusion protein after affinity chromatography on NTA-agarose; lane 4, thrombin-cleaved histidine-leader Hmpl polypeptide; lane 5, native Hmpl polypeptide purified from *U. maydis*; lane 6, crude acid soluble *U. maydis* extract; lane 7, native Hmpl polypeptide purified from *U. maydis* (5 µg); lane 8, protein standards; and lane 9, prestained protein standards. Molecular masses of protein standards are indicated at the right of the figure and calculated masses of the histidine-leader Hmp1 fusion protein, the thrombin cleaved histidine-leader Hmp1 polypeptide, and native Hmpl polypeptide are indicated at the left of the figure, respectively.

Sequence analysis also indicated that each of the clones contained a single complete open reading frame within the cDNA tract. The deduced protein sequence predicted a polypeptide 98 residues in length with a mass of 10,151 Da, in close agreement with the size (11 kDa) estimated from the electrophoretic mobility obtained in analysis of the native *Ustilago maydis* cruciform binding protein (FIG. 3). In addition, the two peptides (SEQ ID NOS: 23 and 4) whose sequences had been obtained empirically from automated sequencing of tryptic peptides were both matched to blocks of residues found in the deduced amino acid sequence.

The genomic sequence of the HMP1 gene was obtained after PCR amplification of genomic *U. maydis* DNA using oligonucleotide primers corresponding to the translational start site and the inverse complement of the termination site. These primers were: 5'GCGGATCCCAAGGAGTCA-CAATGTCTGAGC (SEQ ID NO: 7) and 5'GCGGATC-CGTTTAGGAGTTGA (SEQ ID NO: 8). In addition, for cloning purposes, the primers were designed with BamHI restriction sites. The resulting amplified fragment isolated after PCR amplification was then inserted into the pBluescript II SK+ plasmid vector, and the nucleotide sequence of the clone was determined according to standard methods. Sequence analysis revealed that the amplified fragment contained the identical sequence determined for the HMP1 cDNA except for a 91 bp intron present near the 5' end of the gene (shown in FIG. 2).

This gene was termed HMP1, meaning first <u>h</u>elix <u>m</u>odification recognition <u>p</u>rotein.

Overexpression and Purification of the Hmp1 Polypeptide

The Hmp1 polypeptide was overexpressed in *E. coli* as a hexa-histidine fusion protein and purified as follows.

The cDNA coding segment of the HMP1 gene was amplified as a cassette containing terminal BamHI restriction sites employing the primers described above (SEQ ID NOS: 7 and 8). The PCR-amplified HMP1 cassette was then digested with BamHI and subsequently inserted into the pET14b plasmid expression vector (Novagen, Inc., Madison, Wis.). This plasmid construction resulted in the fusion of a leader sequence encoding a hexa-histidine tract of residues to the N-terminus of the Hmp1 polypeptide.

*E. coli* strain HMS174 (F- hsdR recA1Rif$^r$ gal/ λint::lacUV5-T7 gene 1 imm$^{21}$ nin$^5$ Sam$^7$) lysogenized with λDE3 and harboring pLysS (Novagen, Inc., Madison, Wis.) was then transformed with the pET14b/HMP1 plasmid expression vector. Cell cultures (500 ml) expressing the hexa-histidine Hmp1 polypeptide fusion were grown in LB medium containing 100 µg/ml ampicillin at 37° C. to a density of 2×10$^8$ cells/ml and induced by addition of 0.2 mM isopropyl-thio-β-D galactoside (IPTG) according to standard methods. After 2.5 hours, the cells were harvested by centrifugation, resuspended in 15 ml of 20 mM Tris-HCl, pH 7.9 and 0.5 M NaCl, and lysed by sonication. The broken cell suspension was centrifuged at 10,000×g for 15 minutes, the pellet discarded, and the supernatant containing the hexa-histidine Hmp1 fusion protein applied to a 9 ml column of NTA (nitrilotriacetic acid)-agarose (Qiagen, Inc., Chatsworth, Calif.) charged with Ni$^{2+}$ ions and equilibrated with Buffer A (60 mM imidazole, 20 mM Tris-HCl, 0.5 M NaCl, pH 7.9). After loading, the column was washed with 80 ml of Buffer A. Elution of the Hmp1 fusion protein from the column was performed using a stepwise gradient of Buffer A containing 1 M imidazole. In general, the yield of Hmp1 fusion protein was ≈7.5 mg per 500 ml aliquot of cells.

After dialysis, the hexa-histidine leader sequence was removed by cleavage with 1 unit of thrombin in a standard reaction mixture for 2 hours at 22° C. Dialysis of the reaction mixture against water using Spectra/Por 3 membrane (Spectrum Medical Industries) was sufficient to remove the cleaved leader peptide. Glycerol was then added to 15%, and the purified Hmp1 polypeptide was stored at −70° C. The extinction coefficient of purified Hmp1 polypeptide (calculated from the amino acid composition) was determined to be $7.8 \times 10^3$ M$^{-1}$ cm$^{-1}$.

As shown in FIG. 3, high level production of the 11 kDa hexa-histidine leader-tagged Hmp1 fusion protein was apparent when extracts prepared from IPTG-induced *E. coli* cells were analyzed by SDS-gel electrophoresis (lanes 1 and 2) in a Phastsystem apparatus (Pharmacia, Piscataway, N.J.). The Hmp1 fusion protein remained soluble when cells were crushed and extracted in buffer containing 0.5 M NaCl, and was quantitatively adsorbed when the extract was passed through a column containing an immobilized metal affinity matrix. Elution of the protein with a gradient of imidazole yielded an Hmp1 polypeptide preparation that appeared >95% homogeneous as judged by SDS-gel electrophoresis (FIG. 3, lane 3). As noted above, incubation of the purified Hmp1 fusion protein with thrombin resulted in cleavage of the leader sequence containing the hexa-histidine tract. Removal of the leader sequence was evident by the slight increase in mobility of the protein, also as monitored by SDS-gel electrophoresis (FIG. 3, lane 4).

DNA Binding Assays

The activity of Hmp1 polypeptide was characterized using standard DNA binding assays. In particular, binding reactions of 20 µl containing 20 mM Tris-HCl, pH 7.5, 10 mM MgCl$_2$, 1 mM EDTA, 50 mM KCl, $^{32}$P-labeled DNA, and purified recombinant or purified *Ustilago maydis* Hmp1 polypeptide were utilized. Reactions were conducted at 30° C. for 30 minutes. Formation of protein-DNA complexes was determined by either nitrocellulose filter retention assays or gel mobility shift assays according to standard methods. For the former, reaction mixtures were spotted directly onto a nitrocellulose filter which had been previously soaked in the reaction buffer and held in a vacuum filter manifold. Filters were washed with two 1 ml aliquots of buffer, dried, and the radioactivity determined by scintillation counting. For the latter method, 2 µl of tracking dye solution containing 10% glycerol was added, and the mixture was then loaded onto an 8% polyacrylamide gel containing 50 mM Tris base, 50 mM boric acid and 0.5 mM EDTA. Electrophoresis of the reaction mixtures was carried out until the tracking dye had migrated about 10 cm. The resulting gel was dried onto a piece of Whatman 3MM paper and autoradiographed according to standard methods. Autoradiographic images were digitized using a Microtek scanner, and the images were processed using Adobe computer software.

Oligonucleotide Substrates

Three different types of DNA substrates were utilized in Hmp1 polypeptide binding reactions. These were (i) cruciform substrates generated by annealing oligonucleotides with internal sequences containing unique self-complementary stretches of nucleotides, (ii) linear DNA duplexes containing at least a single mismatched base pair, and (iii) hairpin oligonucleotides containing a centrally placed single mismatched base pair. Oligonucleotides were synthesized by standard techniques. The DNA substrates are shown schematically in FIGS. 1A–C.

Cruciform DNA substrates were prepared by annealing two 61-mer oligonucleotides with the following sequences:
5'GTCTAAGCTTAGCTGAATTCGTCTCCGT-GTTTCACGGAGACGAATTTCGATGAGGAT CCATC3' (SEQ ID NO: 9) and 5'TGATGGATCCTCATCGAATTCGTAGGAT-GCTTTGCATCCTACGAATTCAGCTAAGCTT AGA3'(SEQ ID NO: 10). For control duplex DNA, the oligomer of SEQ ID NO: 9 was annealed to the completely complementary oligonucleotide
5'TGATGGATCCTCATCGAATTCGTCTCCGT-GAAACACGGAGACGAATTCAGCTAAGCT TAGA3' (SEQ ID NO: 11). Oligonucleotides used as cruciform substrates were designed with a stretch of 33 residues located in the middle of the oligomer which was self complementary. When the two complementary oligonucleotides were annealed, two unique arms 15 base pairs in length with 3 residue T loops were formed. The two unique arms formed by intermolecular pairing were 13 base pairs in length with a single unpaired residue remaining at the 5' ends (FIG. 1A).

Oligonucleotides used for open-ended DNA duplexes containing single base pair mismatches were prepared as 50-mers which were identical in the forward direction, with the exception of the nucleotide at position 25 which was varied. Reverse direction oligos were completely complementary, except at position 26 which was varied. Annealing of two of the following forward and reverse oligonucleotides resulted in the formation of completely paired duplexes, with the exception of a single mismatch located in the middle of the molecule. The length of these test duplexes was chosen for convenience; mismatch detection may be accomplished using DNA substrates of increased length, if desired.

When self-annealed, these oligonucleotides formed hairpins 15 base pairs in length with a loop of three T residues at the hairpin ends and 1 residue unpaired at the 5' end. The underlined nucleotides in bold indicate the mismatched base pairs.

Cruciform and open-ended linear duplex substrates were prepared by denaturing equimolar mixtures of the appropriate complementary pair of oligonucleotides at 100° C. for 1 minute, annealing at 65° C. for 3 hr, followed by slow cooling to room temperature. All oligonucleotides were labeled at the 5' end with T4 polynucleotide kinase and [$\gamma$-$^{32}$P]ATP. Unincorporated label was removed by centrifugation through Sephadex G25 spin columns (Boehringer Mannheim, Indianapolis, Ind.). DNA substrates for use in binding reactions were purified by electrophoresis in 8% polyacrylamide gels containing 100 mM Tris base, 100 mM boric acid, and 1 mM EDTA, eluted from isolated gel slices, and concentrated after precipitation in ethanol. Specific activities for all oligonucleotides ranged from $10^3$ to $10^4$ cpm per pmole.

Cruciform Binding Activity of Hmp1 Polypeptide

Cruciform binding activity of purified recombinant Hmp1 polypeptide was examined using a nitrocellulose filter retention assay performed according to the method of Kotani et al. (*Chromosoma* 102: 348–354, 1993), with the exception that two oligonucleotides, each with a unique internal stretch of tandem inverted complementary sequences (FIG. 1A), were used as substrates. When these two oligonucleotides Forward:

5'GCAGTGTCCACCAGTCTTGTCCTGGTCTCCATACCTTGATGTACGGATCT3' (SEQ ID NO: 12);

5'GCAGTGTCCACCAGTCTTGTCCTGCTCTCCATACCTTGATGTACGGATCT3' (SEQ ID NO: 13);

5'GCAGTGTCCACCAGTCTTGTCCTGTTCTCCATACCTTGATGTACGGATCT3' (SEQ ID NO: 14);

and

5'GCAGTGTCCACCAGTCTTGTCCTGATCTCCATACCTTGATGTACGGATCT3' (SEQ ID NO: 15).

Reverse:

5'AGATCCGTACATCAAGGTATGGAGACCAGGACAAGACTGGTGGACACTGC3' (SEQ ID NO: 16);

5'AGATCCGTACATCAAGGTATGGAGATCAGGACAAGACTGGTGGACACTGC3' (SEQ ID NO: 17);

5'AGATCCGTACATCAAGGTATGGAGAACAGGACAAGACTGGTGGACACTGC3' (SEQ ID NO: 18);

and

5'AGATCCGTACATCAAGGTATGGAGAGCAGGACAAGACTGGTGGACACTGC3' (SEQ ID NO: 19).

Underlined, bold nucleotides indicate the site involved in the mismatch. Homoduplex controls and duplexes with the desired mismatched base pairs were prepared by annealing the appropriate combinations of forward and reverse oligomers described herein.

Figure 4:
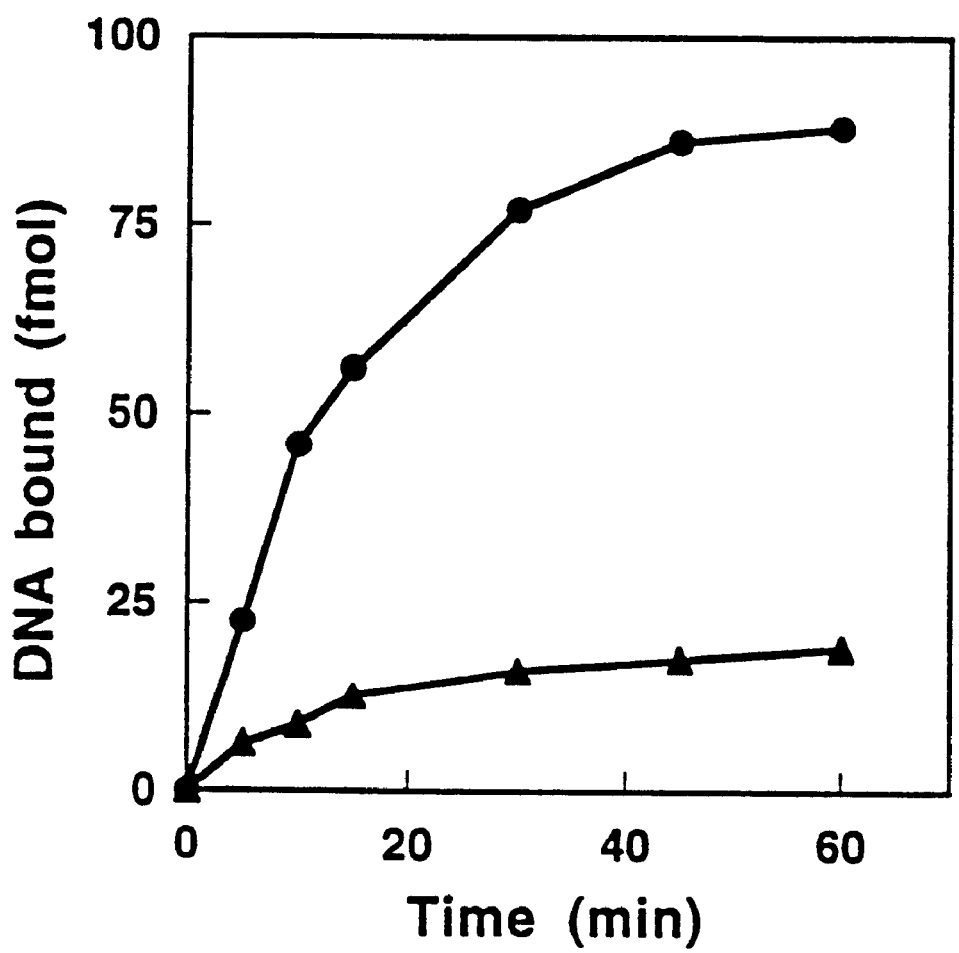
FIG. 4 is a graph showing the DNA binding activity of recombinant Hmp1 polypeptide to cruciform DNA. Reactions (80 μl) containing 2 pmoles of $^{32}$P-labeled cruciform DNA (closed circles) or control duplex DNA (closed triangles) were initiated by addition of 80 pmoles of Hmp1 polypeptide. At the indicated times (0, 20, 40, and 60 minutes), aliquots (20 μl) were removed and washed onto nitrocellulose filters for determination of protein binding.

Hairpin DNA substrates that were perfectly complementary, or which contained one or two mismatched base pairs were prepared by self annealing oligonucleotides of the following sequences:

5'ACAGAATTCTCGGCACTTTGTGCCGAGAA-TTCTG3' (SEQ ID NO: 20);
5'ACAGAATTCTCGGCACTTTCTGCCGATAATT-CTG3' (SEQ ID NO: 21);
5'ACAGAATTCTCGGCACTTTGTGCCGCTAATT-CTG3' (SEQ ID NO: 22).

were annealed, cruciform structures were generated by intramolecular pairing of the inverted complementary sequences and intermolecular pairing between complementary stretches in the flanking sequences. A duplex control was generated by annealing two oligonucleotides with completely complementary sequences. FIG. 4 shows a direct comparison of the binding of Hmp1 polypeptide to radiolabeled cruciform DNA substrate versus linear duplex DNA control. As shown, there was a substantial margin in the rate and extent of binding of Hmp1 polypeptide to the cruciform substrate.

Binding of Hmp1 Polypeptide to DNA with Mismatched Base Pairs

To assess the binding activity of Hmp1 polypeptide to mismatched bases, a standard nitrocellulose filter assay was utilized. DNA duplex substrates were designed containing a single C/T mismatched base pair in the middle of the sequence and were formed by the annealing of two complementary oligonucleotides 50 residues in length (FIG. 1B). Hmp1 polypeptide:DNA duplex complex formation was monitored by assaying the retention of radiolabeled DNA on nitrocellulose filters as described above. In addition, DNA binding of Hmp1 polypeptide was examined under different ionic conditions by direct comparison of the binding activities between $^{32}$P-labeled mismatched DNA substrate and control $^{32}$P-labeled homoduplex substrate.

Figure 5:
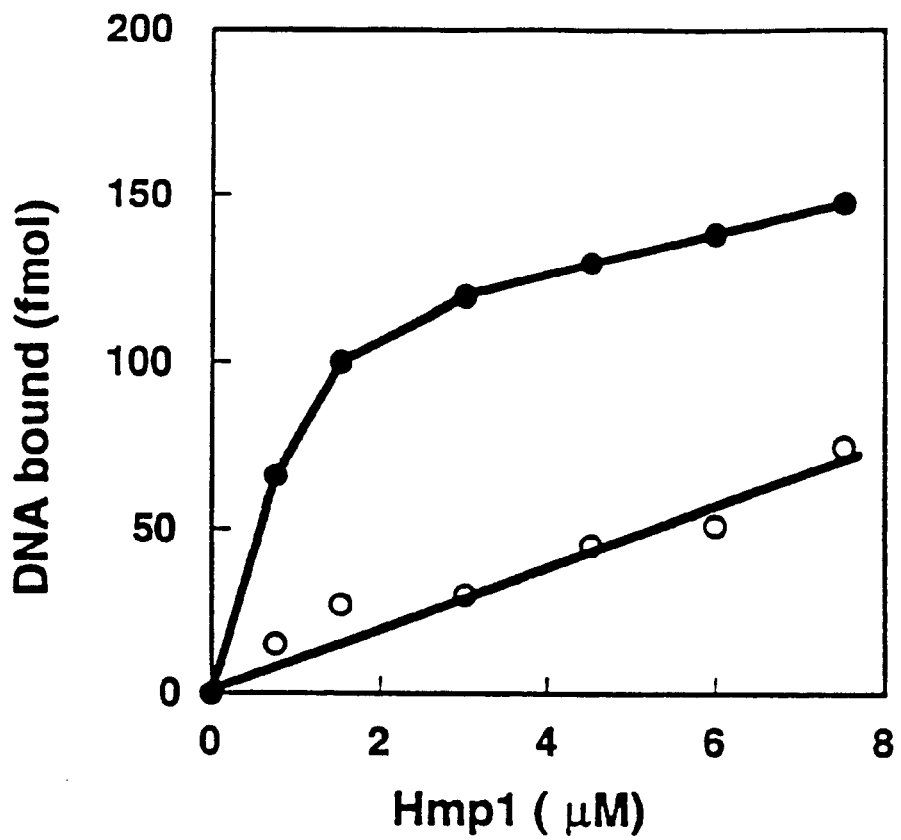
FIG. 5 is a graph showing the binding of recombinant Hmp1 polypeptide to an open-ended DNA duplex containing mismatched base pairs. Reactions (20 μl) contained open-ended linear $^{32}$P-labeled DNA duplex substrates (50-mer duplexes) as shown in FIG. 1B at a concentration of 15 nM. Hmp1 polypeptide was added to the reaction mixture at the indicated concentrations. After 30 minutes at 30° C., the reaction mixtures were passed through nitrocellulose filters, and the DNA retained on each filter was determined by scintillation counting. In this graph, closed circles represent heteroduplex DNA with a single C/T mismatch; open circles represent homoduplex control.
Figure 6:
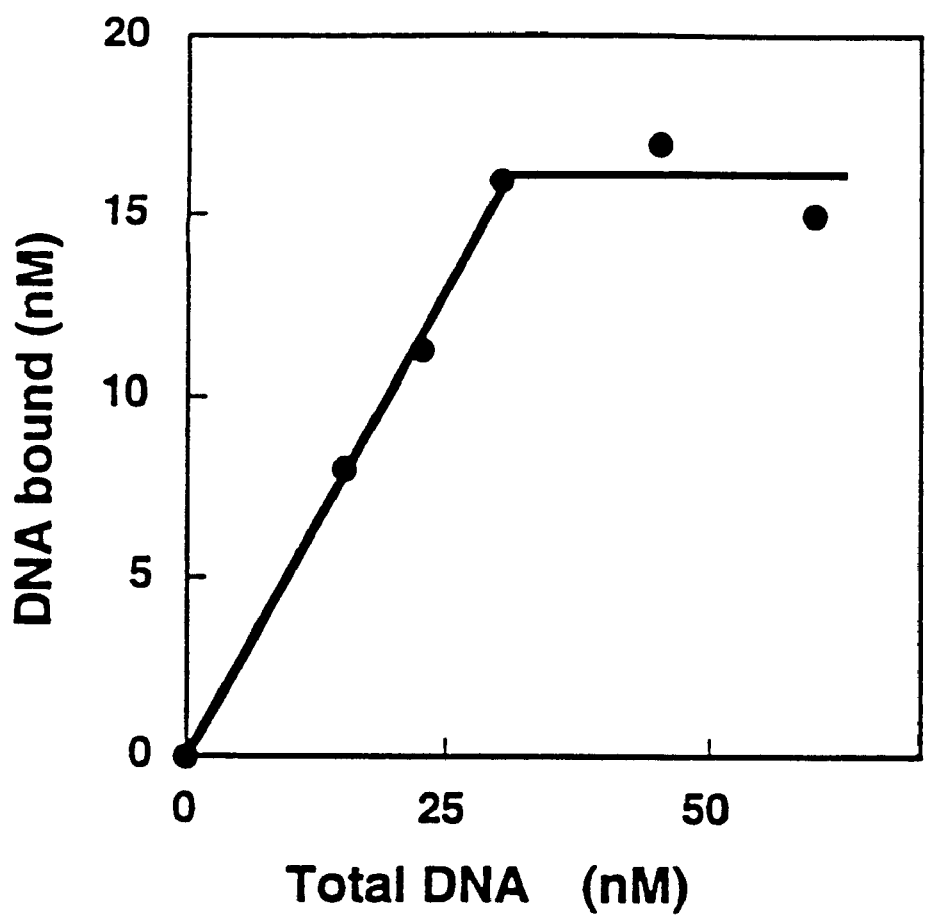
FIG. 6 is a graph showing a recombinant Hmp1 polypeptide binding isotherm with mismatch-containing heteroduplex DNA. Reactions (20 μl) contained 2.3 μM Hmp1 polypeptide and the indicated concentrations of 50-mer heteroduplex DNA with a C/T mismatch at position 25. After 30 minutes at 30° C., reaction mixtures were passed through nitrocellulose filters, and the heteroduplex DNA retained on the filter was determined by scintillation counting.

As shown in FIG. 5, with increasing concentrations of Hmp1 polypeptide, there developed a marked preference in binding to a mismatched DNA substrate over a homoduplex control. This differential was the same regardless of whether 10 mM $Mg^{2+}$ was present or absent in the reaction mixture. Maximal binding was observed within 30 minutes and did not change significantly over longer periods of incubation. In addition, the binding of Hmp1 polypeptide to DNA substrates was generally insensitive to salt. For example, with 0.25 M NaCl present, binding of Hmp1 polypeptide was reduced by half. Binding to the mismatched DNA substrate with a fixed level of protein and an increasing concentration of oligonucleotide substrate appeared to correspond to a classical saturation process (FIG. 6). Half saturation was reached when the mismatched DNA substrate was at ≈15 nM. Scatchard analysis, however, indicated that the mode of Hmp1 polypeptide binding was complex.

Figure 7:
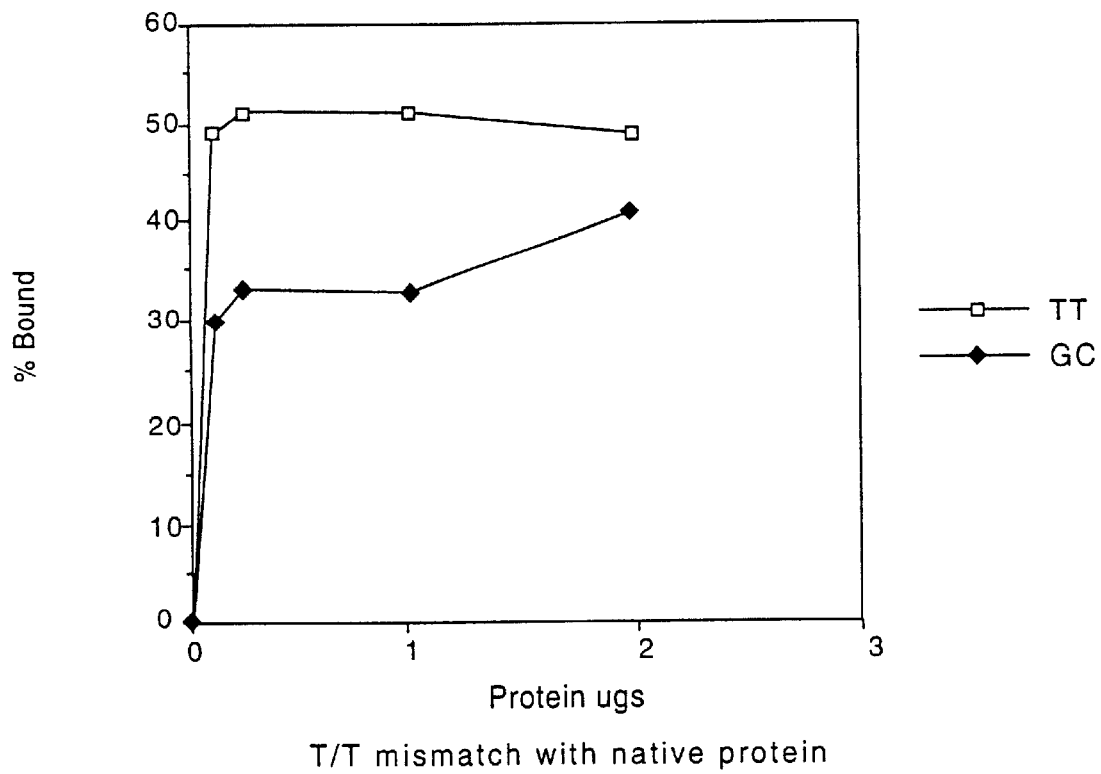
FIG. 7 is a graph showing Hmp1 polypeptide binding to either a homoduplex DNA substrate ("G/C") or to a heteroduplex substrate that includes a T/T mismatch ("T/T"). Experiments were carried out as described in FIG. 5, except that the Hmp1 polypeptide utilized was purified from *Ustilago maydis* by the method of Kotani et al. (*Chromosoma* 102: 348–354, 1993).
Figure 8:
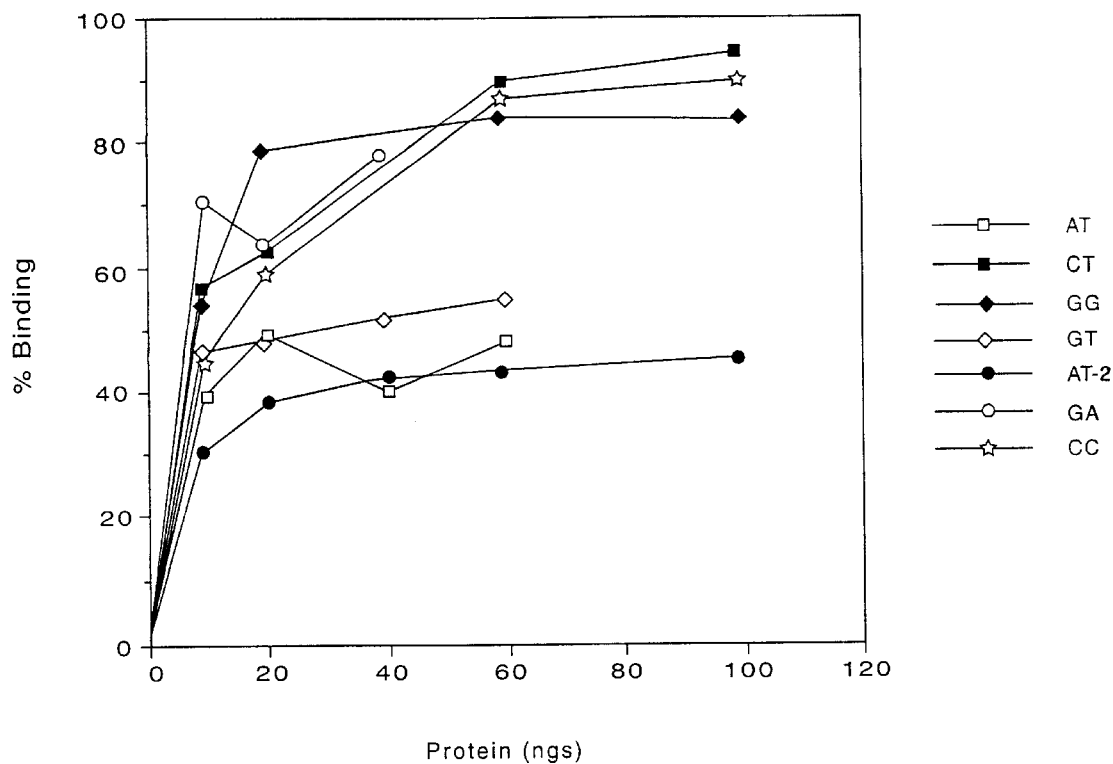
FIG. 8 is a graph showing Hmp1 polypeptide binding to either a homoduplex DNA substrate ("AT" and "AT-2") or to each of a series of mismatch-containing heteroduplex DNA substrates ("CT", "GG", "GT", "GA", and "CC"). Experiments were carried out generally as described in FIG. 5, except that the Hmp1 polypeptide utilized was purified from *Ustilago maydis* by the method of Kotani et al. (*Chromosoma* 102: 348–354, 1993).
Figure 9:
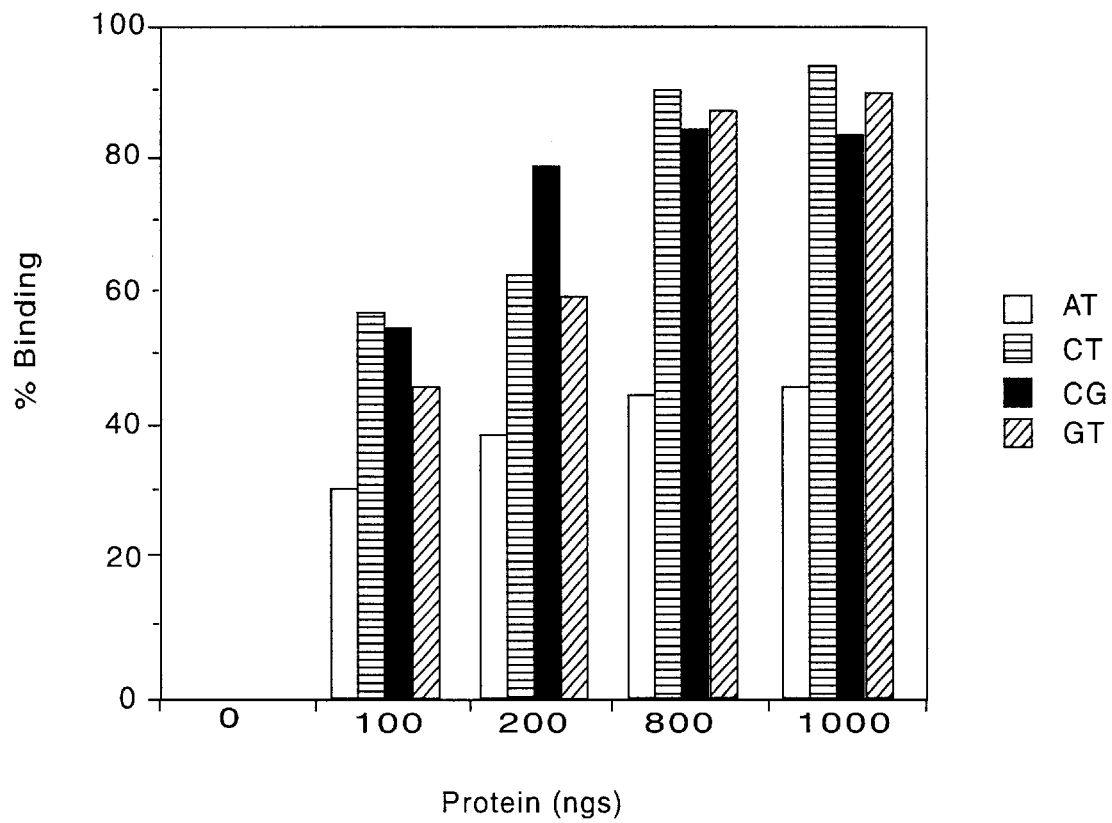
FIG. 9 is a series of bar graphs showing purified *Ustilago maydis* Hmp1 polypeptide binding to either a homoduplex DNA substrate ("AT") or to each of a series of mismatch-containing heteroduplex DNA substrates ("CT", "GG", and "GT"). Experiments were carried out generally as described in FIG. 5.

In a separate set of experiments, the binding of Hmp1 polypeptide to other DNA mismatches was determined using the methods as generally described above. oligonucleotide substrates containing a series of different mismatches were prepared and tested for Hmp1 polypeptide binding using filter binding assays. As shown in FIGS. 7–9, in comparison to homoduplex (A/T or G/C) substrates, Hmp1 polypeptide purified from *Ustilago maydis* preferentially bound each mismatch-containing heteroduplex substrate tested. In particular, FIG. 7 demonstrates that Hmp1 polypeptide exhibited preferential binding to heteroduplexes that included a T/T mismatch, and FIG. 8 demonstrated this same result for G/T, G/G, C/C, C/T, and G/A mismatches. FIG. 9 illustrates these same results (in bar graph form) for C/T, G/G, and G/T mismatch binding.

Binding Specificity of Hmp1 Polypeptide to Mismatches

Figure 10:
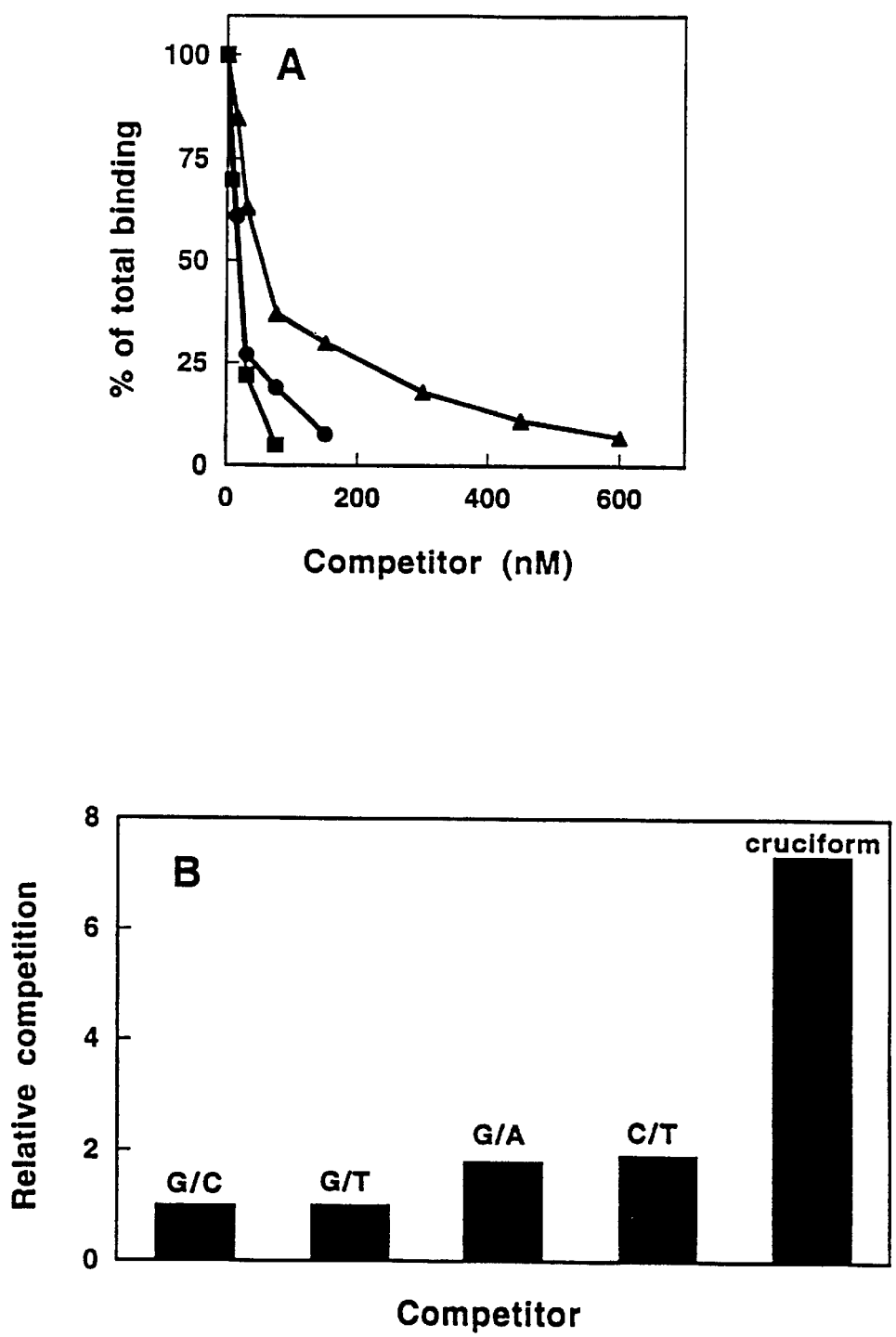
FIGS. 10A–B show a graph and a bar graph illustrating competition assays for binding specificity to heteroduplex DNA containing various single base pair mismatches.

The specificity of Hmp1 polypeptide for binding DNA substrates with different mismatched base pairs was measured using a nitrocellulose filter assay in which the binding of recombinant Hmp1 polypeptide to $^{32}$P-labeled mismatched substrate was measured in the presence of unlabeled oligonucleotide substrate competitors. Discrimination between two competitors was determined by measuring the maximal separation between binding curves along the coordinate representing competitor concentration, as described by Chi and Kolodner (*J. Biol. Chem.* 269, 29984–29992, 1994). Using this method, it was observed that a 4-fold higher level of homoduplex competitor was required to achieve the same level of competition for a $^{32}$P-labeled C/T mismatch substrate as was observed with the unlabeled C/T mismatch competitor (FIG. 10A). In addition, it was observed that cruciform DNA substrate was 7.5-fold more effective as a competitor than the C/T mismatch competitor.

The relative ranking of the effectiveness of other competitor substrates (e.g., G/T and G/A mismatches) was determined by comparison at a standardized level of competitor, also as described by Chi and Kolodner (*J. Biol. Chem.* 269, 29984–29992, 1994). This concentration was fixed by the point of the largest differential between the homoduplex and C/T mismatch competitor and was taken as 75 nM. Competition with a G/T mismatch was no more effective than homoduplex control DNA, but competition with a G/A mismatch was equal in effectiveness to C/T competition (FIG. 10B).

Figure 11:
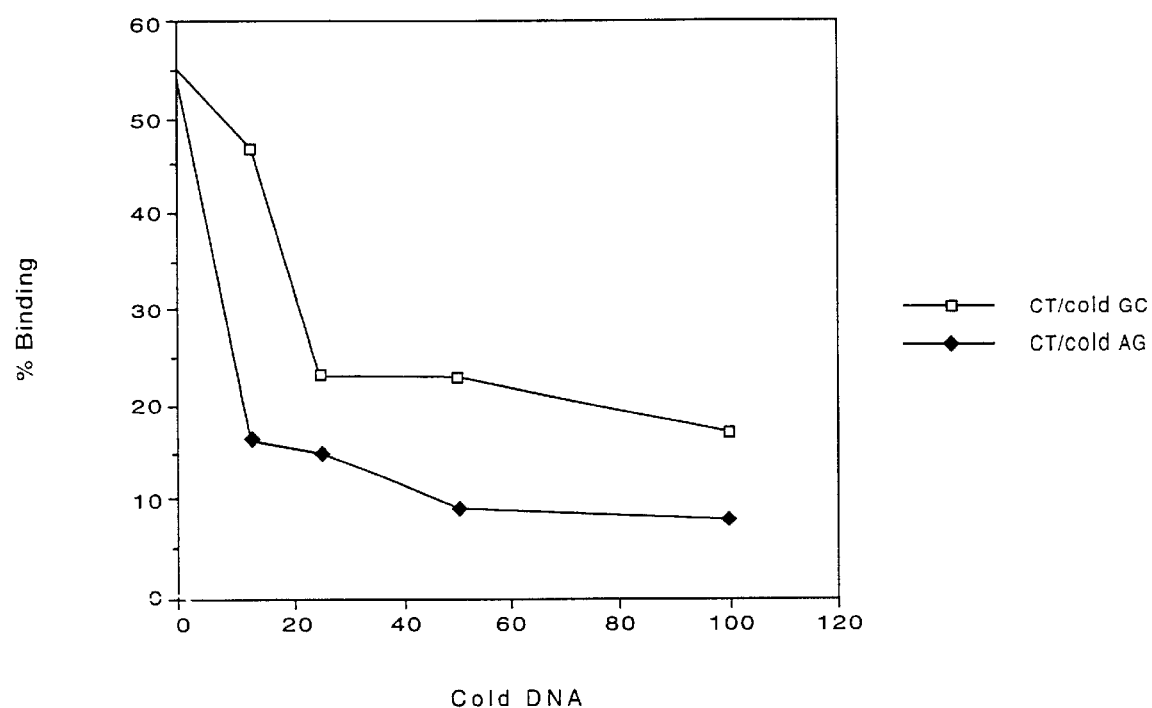
FIG. 11 is a graph illustrating a competition assay for binding specificity to heteroduplex DNA containing a C/T mismatch. Open squares represent competition by a homoduplex sequence, and closed circles represent competition by a heteroduplex sequence that includes an A/G mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 12:
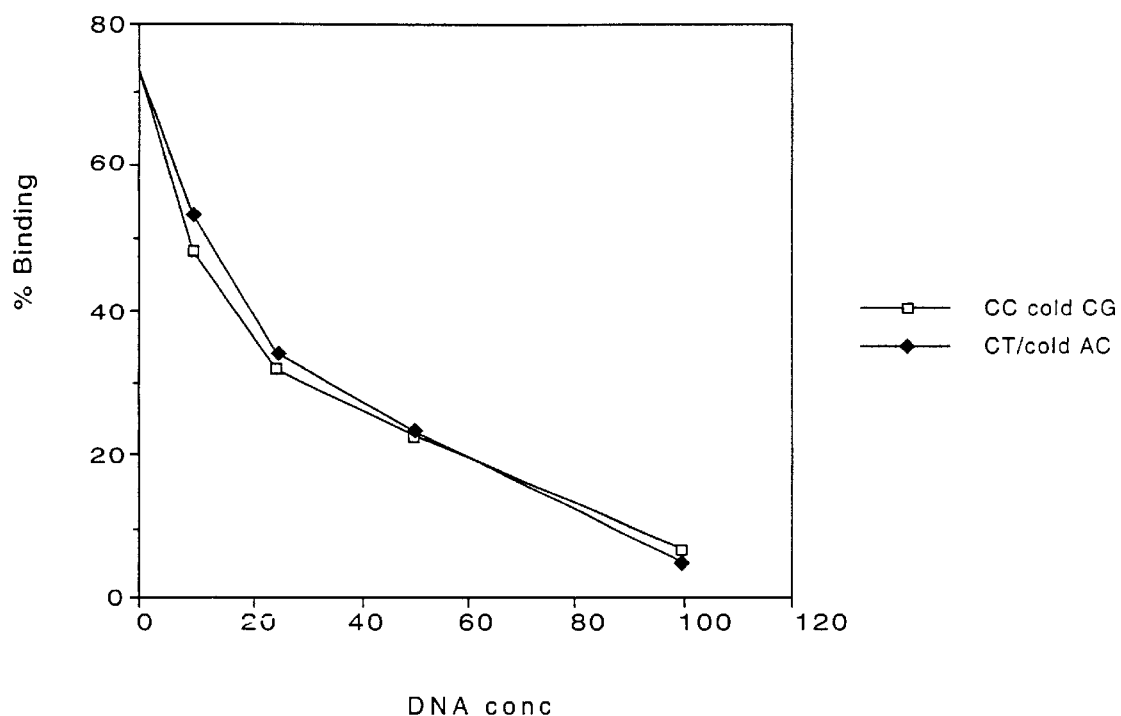
FIG. 12 is a graph illustrating a competition assay for binding specificity to heteroduplex DNA containing a C/C mismatch. Open squares represent competition by a homoduplex sequence, and closed circles represent competition by a heteroduplex sequence that includes an A/C mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 13:
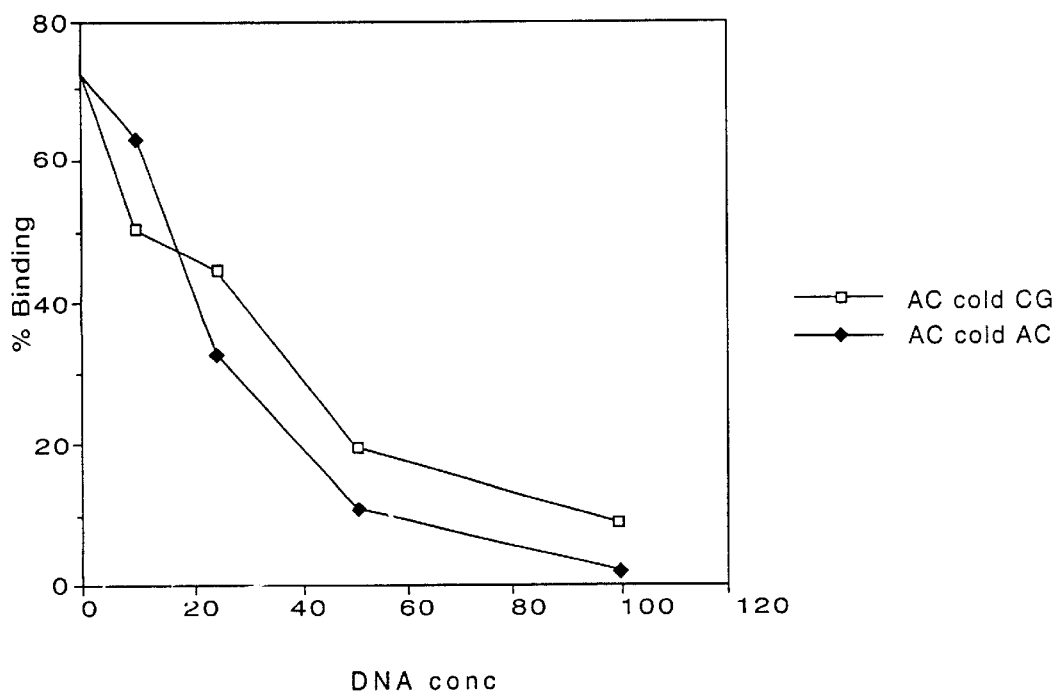
FIG. 13 is a graph illustrating a competition assay for binding specificity to heteroduplex DNA containing an A/C mismatch. Open squares represent competition by a homoduplex sequence, and closed circles represent competition by a heteroduplex sequence that also includes an A/C mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 14:
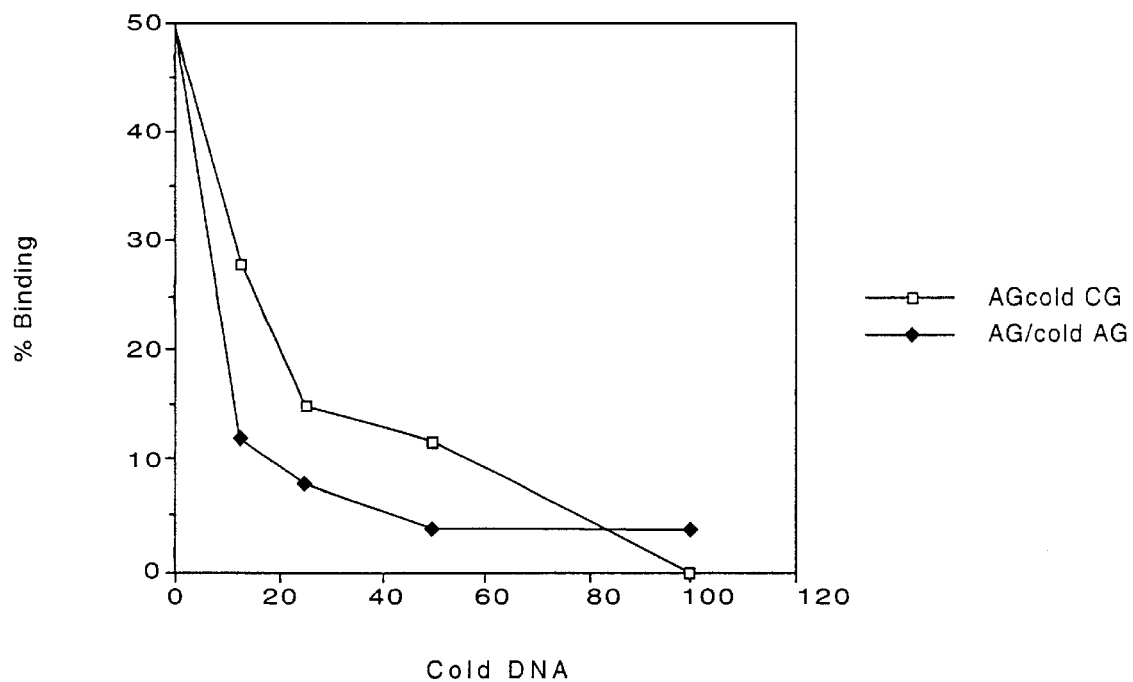
FIG. 14 is a graph illustrating a competition assay for binding specificity to heteroduplex DNA containing an A/G mismatch. Open squares represent competition by a homoduplex sequence, and closed circles represent competition by a heteroduplex sequence that also includes an A/G mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 15:
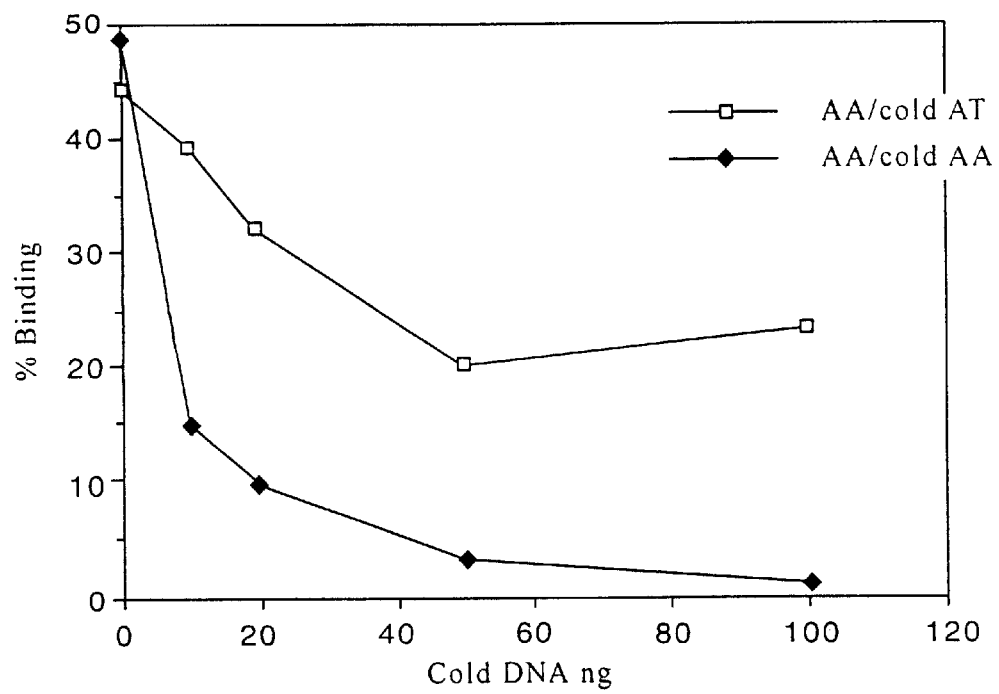
FIG. 15 is a graph illustrating a competition assay for binding specificity to heteroduplex DNA containing an A/A mismatch. Open squares represent competition by a homoduplex sequence, and closed circles represent competition by a heteroduplex sequence that also includes an A/A mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 16:
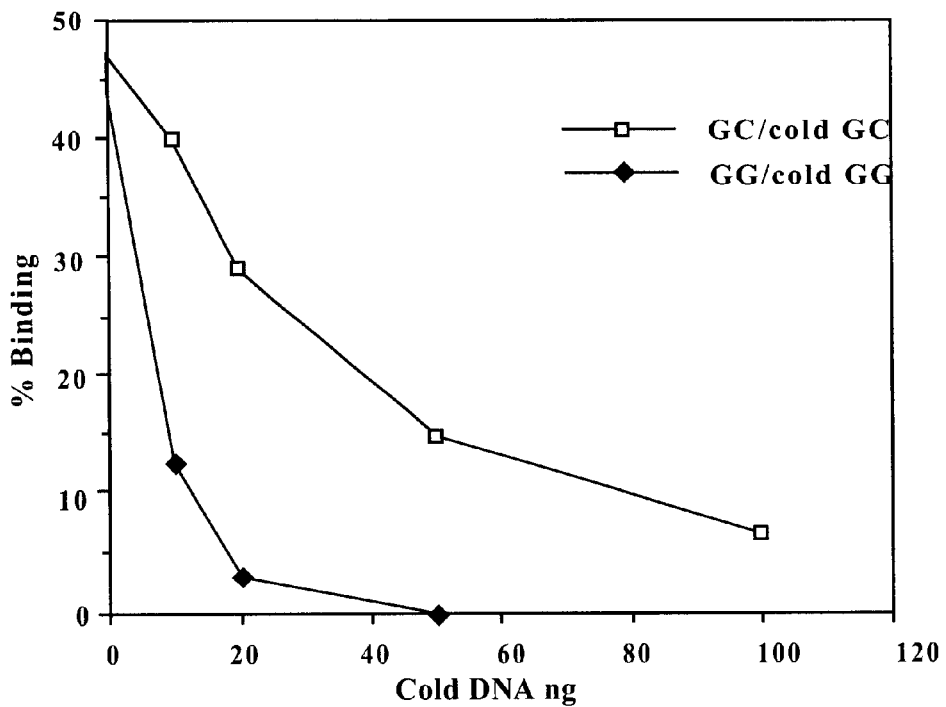
FIG. 16 is a graph illustrating a competition assay for binding specificity to heteroduplex DNA containing a G/G mismatch. Open squares represent competition by a homoduplex sequence, and closed circles represent competition by a heteroduplex sequence that also includes a G/G mismatch. Experiments were carried out generally as described in FIG. 10, except that Hmp1 polypeptide purified from *Ustilago maydis* by the method of Kotani et al. (*Chromosoma* 102: 348–354, 1993) was used in the assay.
Figure 17:
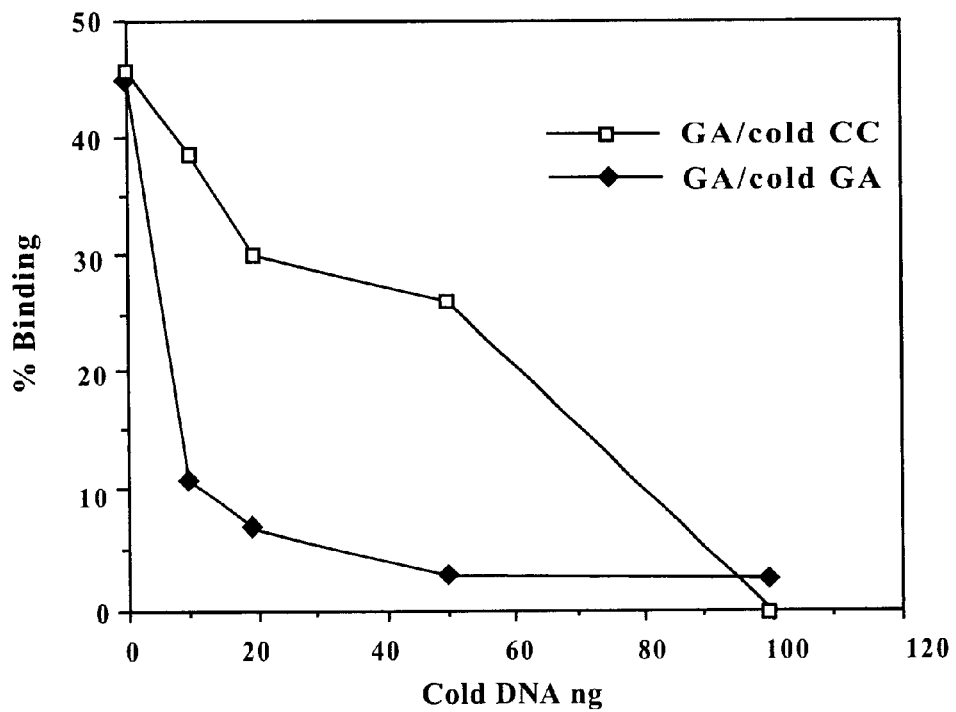
FIG. 17 is a graph illustrating a competition assay for binding specificity to heteroduplex DNA containing a G/A mismatch. Open squares represent competition by a homoduplex sequence, and closed circles represent competition by a heteroduplex sequence that also includes a G/A mismatch. Experiments were carried out generally as described in FIG. 10, except that Hmp1 polypeptide purified from *Ustilago maydis* by the method of Kotani et al. (*Chromosoma* 102:348–354, 1993) was used in the assay.
Figure 18:
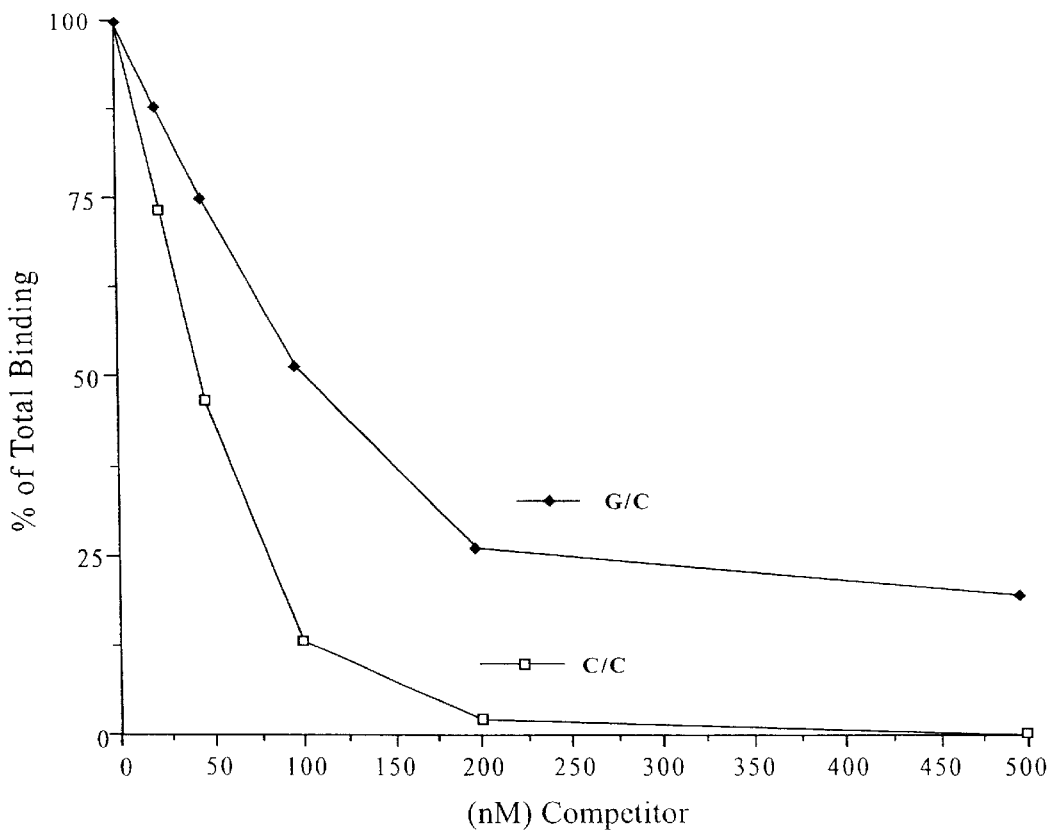
FIG. 18 is a graph illustrating a competition assay for binding specificity to heteroduplex DNA containing a C/C mismatch. Closed circles represent competition by a homoduplex sequence, and open squares represent competition by a heteroduplex sequence that also includes a C/C mismatch. Experiments were carried out generally as described in FIG. 10, using recombinant Hmp1 polypeptide.
Figure 19:
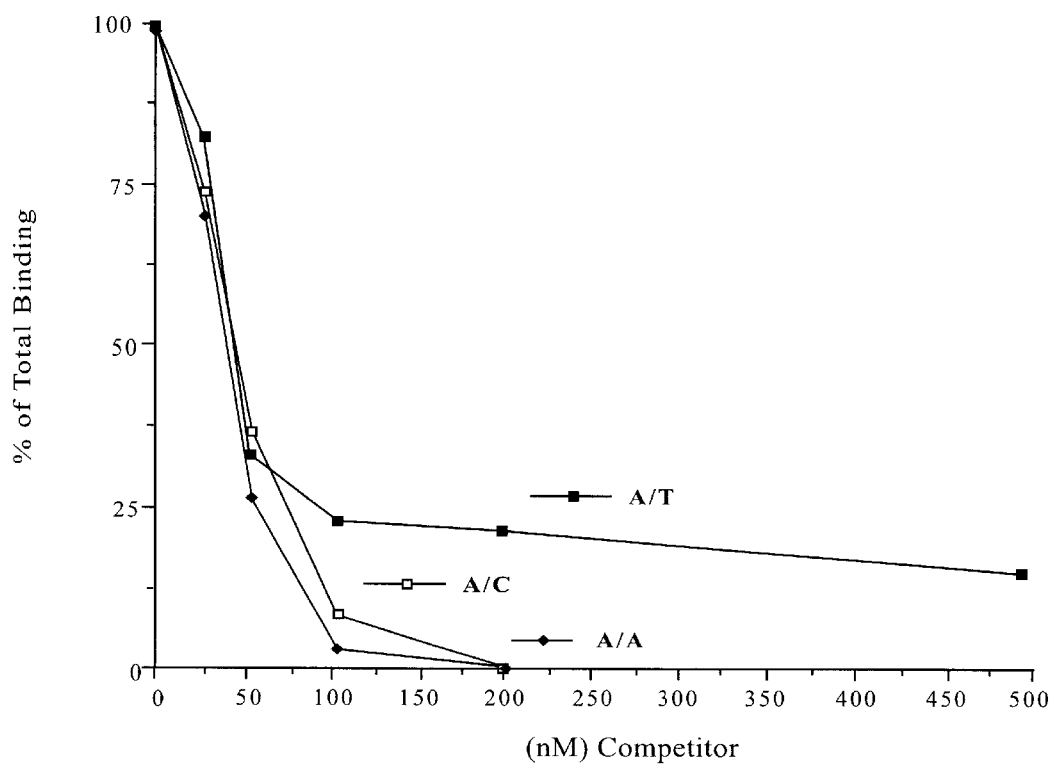
FIG. 19 is a graph illustrating a competition assay for binding specificity to heteroduplex DNA containing either an A/C or an A/A mismatch. Closed squares represent competition by a homoduplex sequence; open squares represent competition of an A/C heteroduplex by an unlabeled A/C heteroduplex; and closed circles represent competition of an A/A heteroduplex by an unlabeled A/A heteroduplex. Experiments were carried out generally as described in FIG. 10, using recombinant Hmp1 polypeptide.
Figure 20:
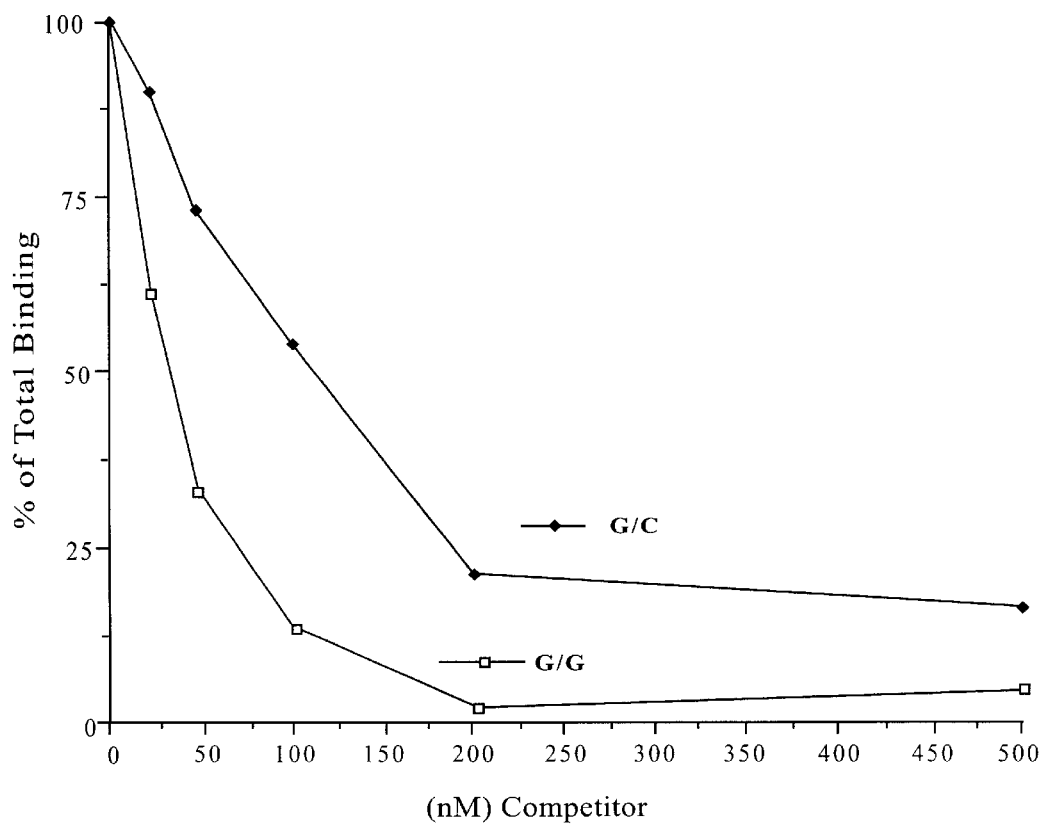
FIG. 20 is a graph illustrating a competition assay for binding specificity to heteroduplex DNA containing a G/G mismatch. Closed circles represent competition by a homoduplex sequence, and open squares represent competition by a heteroduplex sequence that also includes a G/G mismatch. Experiments were carried out generally as described in FIG. 10, using recombinant Hmp1 polypeptide.

In a separate set of experiments, binding by Hmp1 polypeptide (either purified from *Ustilago maydis* or produced recombinantly) was tested for its ability to bind other base pair mismatches, by the methods generally described above (see description of FIG. 10A–B and discussion, supra). The results of these experiments are shown in FIGS. 11–20. In FIG. 11, purified Hmp1 polypeptide was bound to a labeled substrate that included a C/T mismatch, and this complex was competed with either unlabeled homoduplex ("GC") or unlabeled heteroduplex ("AG"). FIG. 11 demonstrates that the heteroduplex competed more effectively for Hmp1 binding than the homoduplex. In FIG. 12, the labeled substrate included a C/C mismatch, and competition was carried out with either unlabeled homoduplex ("CG") or unlabeled heteroduplex ("AC"); here, both the homoduplex and the heteroduplex were able to effectively compete for purified Hmp1 polypeptide. In each of FIGS. 13–17, binding of purified Hmp1 to labeled heteroduplex was competed with either unlabeled homoduplex or an unlabeled heteroduplex that was the same as the labeled substrate. In each of these figures, Hmp1 polypeptide bound the heteroduplex preferentially to a homoduplex substrate. The heteroduplexes tested included each of the following mismatched base pairs: A/C (FIG. 13), A/G (FIG. 14), A/A (FIG. 15), G/G (FIG. 16), and G/A (FIG. 17). In each of FIGS. 18–20, these experiments were repeated using recombinant Hmp1 polypeptide. Again, Hmp1 polypeptide bound mismatch-containing sequences in preference to homoduplex substrates. FIG. 18 shows preferential Hmp1 polypeptide binding to C/C mismatches; FIG. 19 shows preferential binding to A/C and A/A mismatches; and FIG. 20 demonstrates preferential binding to G/G mismatches.

Hmp1 Polypeptide Recognition of Mismatches Precedes Recognition of Hairpins

To assess the relative preference of Hmp1 polypeptide for mismatches as compared to hairpin ends, the binding activity of Hmp1 polypeptide to synthetic oligonucleotides substrates containing a hairpin and a hairpin with mismatches was compared. Substrates were designed as single strands of DNA with self-complementary 15-residue blocks of sequences separated by a string of 3 T residues. When self-annealed, the oligonucleotides form hairpin duplexes with one open end and another capped with a loop by the T residues (FIG. 1C). Using a set of hairpin substrates, one containing a perfectly complementary sequence, a second containing this same sequence with a single C/T mismatch, and a third containing this sequence with a CT/TC two-base pair mismatch, gel mobility shift assays were performed as described above.

Figure 21:
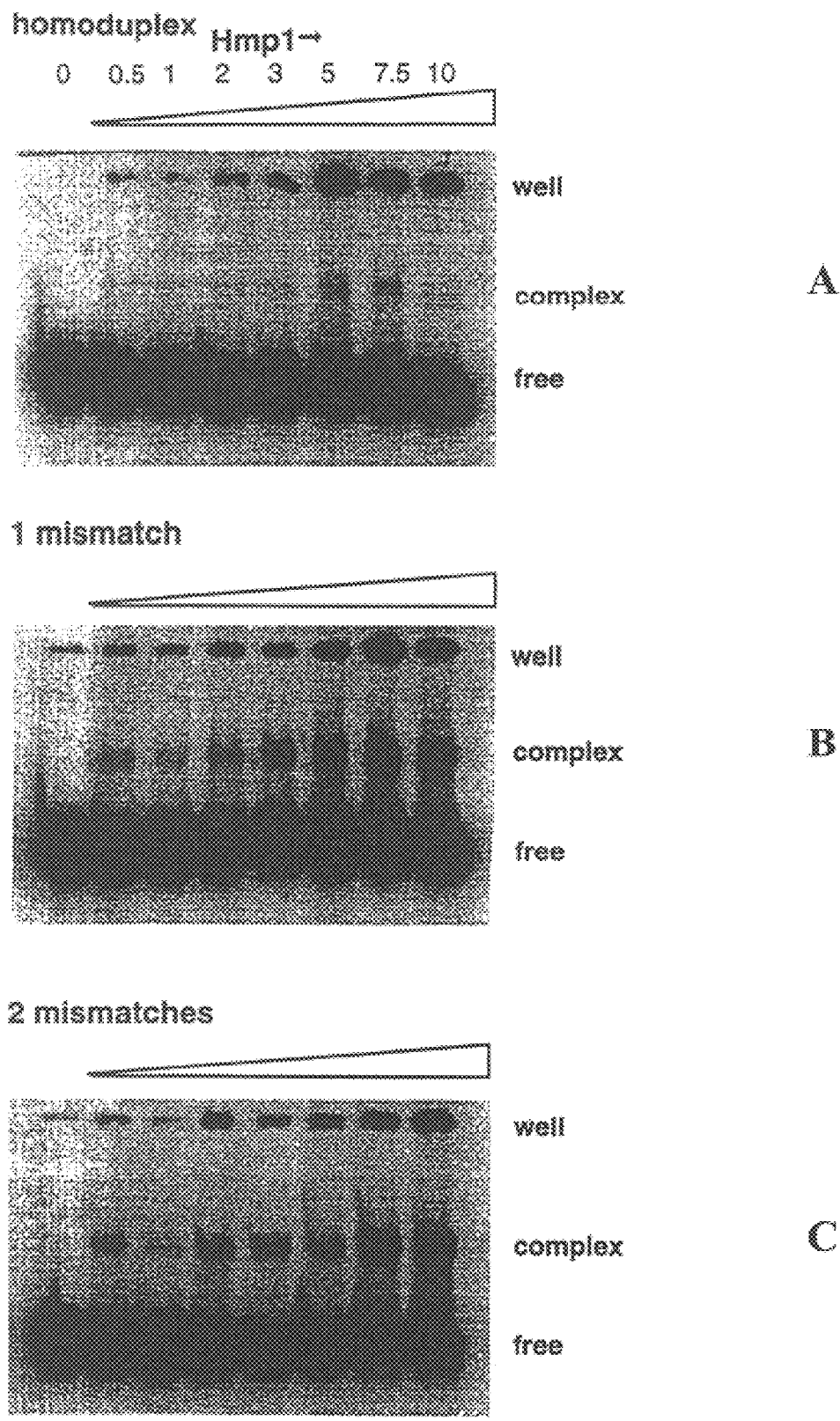
FIGS. 21A–C shows a series of autoradiographs illustrating the binding affinities of Hmp1 polypeptide to homoduplex hairpin DNA (FIG. 21A) and heteroduplex DNA containing either a one base pair mismatch (FIG. 21B) or a two base pair mismatch (FIG. 21C). Reactions (20 μl) contained 1 pmole of $^{32}$P-labeled hairpin or heteroduplex DNA substrates as depicted in FIGS. 1B–C and the indicated level of recombinant Hmp1 polypeptide (in pmoles). After 30 minutes at 30° C., the reaction mixtures were loaded and run in a polyacrylamide gel. Hmp1 polypeptide:DNA complexes are indicated by the bands intermediate in position between free oligonucleotide and radiolabel trapped in the wells.

FIGS. 21A–C show the results of three different gel mobility shift assays for the formation of complexes between hairpin substrates and Hmp1 polypeptide. With increasing levels of Hmp1 polypeptide, a distinct complex with $^{32}$P-labeled homoduplex hairpin DNA became apparent. When substrates with single- or two-base pair mismatches were examined, a complex which was retarded in mobility to the same extent formed with 5- to 10-fold less Hmp1 polypeptide (FIGS. 21A–C). These results indicated that Hmp1 polypeptide bound preferentially to mismatches, as compared to hairpin loops.

Comparison of Hmp1 Polypeptide to Proteins with Related DNA Binding Activities

A search of GenBank and EMBL databases for HMP1-related sequences using BLAST (Atschul et al., *J. Mol. Biol.* 215: 403–410, 1990) and FASTA (Pearson and Lipman, *Proc. Natl. Acad. Sci. USA* 85: 2444–2448, 1988) yielded no obvious matches for homologs. Searches for conserved structural or functional motifs also failed to identify any consensus DNA binding motif of Hmp1 polypeptide.

Unexpectedly, no regions of Hmp1 polypeptide were found to have amino acid identity to the HMG box (Bianchi et al., *EMBO J.* 11: 1055–1063, 1992). The latter encodes a protein domain consisting of an 80 amino acid stretch characterized by a conserved K R P motif at the amino terminus followed by a cluster of hydrophobic amino acids and a number of highly conserved amino acids in the distal half of the 80 residue stretch. HMG-box proteins are known for their ability to introduce sharp bends into DNA and for activity in binding to bent, kinked, or cruciform DNA.

In addition, no homology was observed with proteins having DNA binding properties similar to those of the HMG-box proteins, but with no HMG-box sequence motif. These include proteins HU and integration host factor (IHF) from *E. coli*, the latter of which is known to play an important role in site specific recombination during bacteriophage lambda integration. In addition, these aforementioned proteins are related to each other (Drlica and Rouviere-Yaniv, *Microbiol. Rev.* 51: 301–319, 1987) and have been categorized as HMG-like based on DNA binding activity (Pontiggia et al., *Mol. Microbiol.* 7: 343–350, 1993), but appear fundamentally different from HMG-box containing proteins at the structural level. Solid state and solution studies have revealed that interaction with DNA by proteins with the HMG domain takes place through three α-helices (Werner et al., *Cell* 81: 705–714, 1995; Weir et al., *EMBO J.* 12: 1311–1317, 1993; reviewed in Grosschedl et al., *Trends Genet.* 10: 94–100, 1994) while the HU/IHF family appears to contact DNA through two β-sheet ribbons (Yang and Nash, *Cell* 57: 869–880, 1989).

Comparisons between the Hmp1 polypeptide and the translations of hupA and hupB, the structural genes for HU, himA and hip, the structural genes for IHF, and RuvA, the Holliday junction recognition protein, revealed no significant overall homology. In addition, comparisons between Hmp1 polypeptide and various proteins reported to be active in binding DNA with mismatched bases (e.g., RecA protein (Wang et al., *J. Biol. Chem.* 268: 17571–17577, 1993), human p53 (Lee et al., *Cell* 81: 1013–1020, 1995), and yeast Msh2 (Alani et al., *Genes & Develop.* 9: 234–247, 1995)) failed to reveal significant stretches of homology, with the exception of a 120 amino acid residue stretch at the carboxy terminus of RecA protein (FIG. 22).

Based on the above experiments, at least three unexpected findings emerged. First, Hmp1 polypeptide was found to recognize and bind to DNA with cruciform structures and also to bind preferentially to heteroduplex DNA containing any, single mismatched base pair. Second, the Hmp1 polypeptide appeared to be unrelated to any of the well-known HMG type architectural proteins. Finally, unlike Mut proteins which most efficiently recognize G/T mismatches, Hmp1 polypeptides preferentially bound C/T mismatches and bound all other mismatches, including C/C mismatches, even under standard solution conditions.

Isolation of Other HMP cDNAs and Genomic DNAs

Based on the isolation described herein of the novel Hmp1 gene and polypeptide, the isolation of additional Hmp coding sequences is made possible using standard techniques well known in the art. For example, using all or a portion of the amino acid sequence of an Hmp1 polypeptide of the invention, one may readily design HMP-specific oligonucleotide probes, including HMP degenerate oligonucleotide probes (i.e., a mixture of all possible coding sequences for a given amino acid sequence). These oligonucleotides may be based upon the sequence of either DNA strand and any appropriate portion of the HMP sequence. General methods for designing and preparing such probes are provided, for example, in Ausubel et al., *Current Protocols in Molecular Biology*, Wiley Interscience, New York, and Berger and Kimmel, *Guide to Molecular Cloning Techniques*, 1987, Academic Press, New York. These oligonucleotides are useful for HMP gene isolation, either through their use as probes capable of hybridizing to HMP complementary sequences or as primers for various amplification techniques, for example, polymerase chain reaction (PCR) cloning strategies.

Hybridization techniques and procedures are well known to those skilled in the art and are described, for example, in Ausubel et al. (supra); Berger and Kimmel (supra); and Sambrook et al., *Molecular Cloning: A Laboratory Manual*, Cold Spring Harbor Laboratory Press, New York. If desired, a combination of different oligonucleotide probes may be used for the screening of a recombinant DNA library. The oligonucleotides may be detectably-labeled using methods known in the art and used to probe filter replicas from a recombinant DNA library. Recombinant DNA libraries are prepared according to methods well known in the art, for example, as described in Ausubel et al. (supra), or they may be obtained from commercial sources.

For detection or isolation of closely related HMP sequences, high stringency conditions are preferably used; such conditions include hybridization at about 42° C. and about 50% formamide, a first wash at about 65° C., about 2×SSC, and 1% SDS, followed by a second wash at about 65° C. and about 0.1% SDS, and 1×SSC. Lower stringency conditions for detecting HMP genes having about 85% sequence identity to the HMP gene described herein include, for example, hybridization at about 42° C. in the absence of formamide, a first wash at about 42° C., about 6×SSC, and about 1% SDS, and a second wash at about 50° C., about 6×SSC, and about 1% SDS. These stringency conditions are exemplary; other appropriate conditions may be determined by those skilled in the art.

As discussed above, HMP oligonucleotides may also be used as primers in amplification cloning strategies, for example, using PCR. PCR methods are well known in the art and are described, for example, in *PCR Technology*, Erlich, ed., Stockton Press, London, 1989; *PCR Protocols: A Guide to Methods and Applications*, Innis et al., eds., Academic Press, Inc., New York, 1990; and Ausubel et al. (supra)). Primers are optionally designed to allow cloning of the amplified product into a suitable vector, for example, by including appropriate restriction sites at the 5' and 3' ends of the amplified fragment (as described herein). If desired, HMP may be isolated using the PCR "RACE" technique, or Rapid Amplification of cDNA Ends (see, e.g., Innis et al. (supra)). By this method, oligonucleotide primers based on an HMP sequence are oriented in the 3' and 5' directions and are used to generate overlapping PCR fragments. These overlapping 3'- and 5'-end RACE products are combined to produce an intact full-length cDNA. This method is described in Innis et al. (supra); and Frohman et al., *Proc. Natl. Acad. Sci. USA* 85: 8998, 1988.

Useful HMP sequences may be isolated from any appropriate organism. Confirmation of a sequence's relatedness to the Hmp polypeptide family may be accomplished by DNA sequencing and comparison, for example, to the HMP1 sequence described herein.

Hmp Polypeptide Expression

An Hmp polypeptide according to the invention may be expressed following transformation of a suitable host cell with all or a part of an Hmp polypeptide-encoding cDNA fragment (e.g., the cDNA described herein) in a suitable expression vehicle. As is discussed below, if desired, an Hmp polypeptide according to the invention may be expressed as part of a gene fusion (e.g., a hexa-histidine-Hmp polypeptide, strepdavidin-Hmp polypeptide, or protein A-Hmp polypeptide fusion).

Those skilled in the field of molecular biology will understand that any of a wide variety of expression systems may be used to provide the recombinant protein in either a fused or non-fused form. For example, an Hmp polypeptide may be produced in a prokaryotic host (e.g., *E. coli*) or in a eukaryotic host (e.g., *Saccharomyces cerevisiae, Ustilago maydis*, or mammalian cells). Such cells are available from a wide range of sources (e.g., the American Type Culture Collection, Rockland, Md.; see also Ausubel et al. (supra)). The method of transformation and the choice of expression vehicle will depend on the host system selected. Transformation methods are described, e.g., in Ausubel et al. (supra); expression vehicles may be chosen from those provided, e.g., in *Cloning Vectors*: A Laboratory Manual (P.H. Pouwels et al., 1985, Supp. 1987).

One preferred expression system for Hmp polypeptide production is the *E. coli* pET expression system (Novagen, Inc., Madison, Wis.). According to this method, DNA encoding an Hmp polypeptide is inserted into a pET vector in an orientation designed to allow expression. Since the HMP gene is under the control of the T7 regulatory signals, expression of HMP is induced by inducing the expression of T7 RNA polymerase in the host cell. This is typically achieved using host strains which express T7 RNA polymerase in response to IPTG induction. Once produced, recombinant Hmp polypeptide is then isolated according to standard methods known in the art.

Alternatively, Hmp polypeptides may be produced in mammalian systems. Vectors suitable, for example, for stable transfection of mammalian cells are available to the public (see, for example, Pouwels et al. (supra)), and methods for constructing such cell lines are also publicly available (see, e.g., Ausubel et al. (supra)). In one particular example, cDNA encoding an Hmp polypeptide is cloned into an expression vector which includes the dihydrofolate reductase (DHFR) gene. Integration of the plasmid and, therefore, the Hmp polypeptide-encoding gene into the host cell chromosome is selected for by inclusion of 0.01–300 $\mu$M methotrexate in the cell culture medium (as described in Ausubel et al., supra). This dominant selection technique can be accomplished in most cell types.

If desired, recombinant protein expression may be increased by DHFR-mediated amplification of the transfected gene. Methods for selecting cell lines bearing gene amplifications are described in Ausubel et al. (supra); such methods generally involve extended culture in medium containing gradually increasing levels of methotrexate. DHFR-containing expression vectors commonly used for this purpose include pCVSEII-DHRF and pAdD26SV(A) (described in Ausubel et al., supra). A DHFR-deficient CHO cell line (e.g., CHO DHFR⁻ cells, ATCC Accession No. CRL 9096) is among the host cells preferred for DHFR selection of a stably-transfected cell line or DHFR-mediated gene amplification.

Once a recombinant Hmp polypeptide is expressed, it is isolated, e.g., using affinity chromatography. In one example, isolation is facilitated by inclusion in the Hmp polypeptide of a leader sequence or "tag" that allows Hmp polypeptide capture (for example, the hexa-histidine leader sequence described herein). In another example, the Hmp polypeptide product is isolated using an anti-Hmp polypeptide antibody (e.g., produced as described below). This antibody may be attached to a solid support (e.g., a column) or may be used in immunoprecipitation methods to bind and isolate the Hmp polypeptide of interest. Lysis and fractionation of Hmp polypeptide-harboring cells prior to affinity chromatography may be performed by any standard method (see, e.g., Ausubel et al., supra). Once isolated, the recombinant protein can, if desired, be further purified, e.g., by high performance liquid chromatography (see, e.g., Fisher, *Laboratory Techniques In Biochemistry And Molecular Biology*, eds., Work and Burdon, Elsevier, 1980). These general techniques of polypeptide expression and purification can also be used to produce and isolate useful Hmp polypeptide fragments or analogs (described below).

Hmp Polypeptide Fusion Proteins

Also included within the invention are Hmp polypeptides fused to one or more additional amino acids. Such fusion proteins may be produced by any standard technique, for example, by recombinant methods, chemical synthesis, or a combination of the two. Fusion proteins may be produced, for example, as a means (i) to increase Hmp polypeptide stability, (ii) to facilitate its purification (for example, by attachment of a removable leader sequence or purification "tag" such as the hexa-histidine leader sequence described herein), (iii) to allow immobilization of an Hmp polypeptide to a solid support by means of an affinity complex (for example, by producing an Hmp fusion protein that includes one member of a specific binding pair, such as streptavidin, biotin, protein A, or an immunoglobulin, or by producing an Hmp polypeptide that includes incorporated cysteine residues for production of disulfide bridges), or (iv) to imbue an Hmp polypeptide with additional functional characteristics (for example, a nucleic acid cleaving function or detectable signal capability). Because Hmp polypeptides may act as monomers, they are well suited to fusion protein production.

In one particular example of a fusion protein according to the invention, Hmp1 is fused to bacteriophage T4 endonuclease VII (Endo VII) to produce a protein that generally and efficiently binds all mismatches (through the Hmp1 portion) and that cleaves at or near the site of a mismatch (through the Endo VII portion). Such a fusion construct may be produced by ligating an Endo VII-encoding fragment (for example, an Ndel/Bam H1-ended fragment) directly downstream from an HMP1 sequence. To remove the HMP1 stop codon and include an Nde1 restriction site, the HMP1 sequence is modified at the carboxy terminus by standard PCR-based techniques. The PCR primers preferably include Ndel sites at both the amino and carboxy ends of HMP1 to allow for the construction of an in frame ATG "start site" at the fusion gene's amino-terminus. The primers also preferably include all nucleotides required in the HMP1 carboxy terminus to facilitate an in frame ligation to the downstream Endo VII fragment. Accuracy of the PCR product may be confirmed by DNA sequencing (for example, automated sequencing using an ABI System).

Once constructed, the fusion gene is cloned into any appropriate expression vector, for example, any overexpression vector. If desired, as described herein, a histidine tag may be incorporated into the amino-terminus of the gene fusion sequence to facilitate protein purification using a nickel agarose column (available, for example, from Novagen or Qiagen). Expression of the fusion protein may be accomplished in any suitable host cell, for example, an *E. coli* cell.

Other examples of useful fusion proteins according to the invention include Hmp polypeptides fused to streptavidin, biotin, protein A, or immunoglobulin. Such fusion proteins may be constructed using publicly available gene sequences and standard techniques.

Antibodies Specific for Hmp Polypeptides

Hmp polypeptides as described herein (or immunogenic fragments or analogues thereof) may be used to raise antibodies useful in the invention; such immunogenic polypeptides may be produced by recombinant or peptide synthetic techniques (see, e.g., *Solid Phase Peptide Synthesis*, supra; Ausubel et al., supra). If desired, the peptides may be coupled to a carrier protein, such as KLH, as described in Ausubel et al, supra. The KLH-peptide is then preferably mixed with an adjuvant (for example, Freund's adjuvant) and injected into guinea pigs, rats, or preferably rabbits to raise a polyclonal antibody preparation. If desired, antibodies may be purified by any standard technique, for example, peptide antigen affinity chromatography.

Monoclonal antibodies may also be prepared using the Hmp polypeptides described above. Standard hybridoma technology is described, e.g., in Kohler et al., *Nature* 256: 495, 1975; Kohler et al., *Eur. J. Immunol.* 6: 511, 1976; Kohler et al., *Eur. J. Immunol.* 6: 292, 1976; Hammerling et al., *In Monoclonal Antibodies and T Cell Hybridomas*, Elsevier, N.Y., 1981; and Ausubel et al., supra.

Once produced, polyclonal or monoclonal antibodies are tested for specific Hmp polypeptide recognition, for example, by Western blot or immunoprecipitation analysis (as described, for example, in Ausubel et al., supra). Antibodies which specifically recognize an Hmp polypeptide are considered to be useful in the invention; such antibodies may be used, e.g., to detect an Hmp polypeptide bound at a site of nucleotide mismatch or to facilitate capture of an Hmp polypeptide:mismatch complex.

Mismatch Detection Using an Hmp Polypeptide

The Hmp polypeptides of the present invention may be used in any standard detection format for the identification of one or more mismatches in a nucleotide sequence. Such formats include any appropriate assay whereby complex formation between an Hmp polypeptide and a mismatch-containing nucleotide sequence may be detected. Formats according to the invention therefore include those that rely on antigen-antibody or nucleic acid probe detection steps and that involve, for example, a labeled test heteroduplex, a labeled Hmp polypeptide, a labeled Hmp polypeptide-specific antibody, or a labeled heteroduplex-specific nucleotide probe. Formats according to the invention may also involve indirect detection of an Hmp polypeptide:mismatch complex (for example, by using a second labeled probe or a second labeled antibody). In addition, any appropriate label which may be directly or indirectly visualized may be utilized in these detection assays including, without limitation, any radioactive, fluorescent, colored, or chemiluminescent label, or a hapten (for example, digoxigenin) which may be visualized using a labeled, hapten-specific antibody. Hmp polypeptide:mismatch complex formation may also be detected (and the mismatch site localized) using any standard DNA protection assay, for example, by footprinting-type analysis involving, for example, a unidirectional exonuclease (such as T7 DNA polymerase).

In one particular example of a useful detection format according to the invention, an Hmp polypeptide is first immobilized on a solid support (for example, a filter, bead, magnetic bead (such as a Dynabead, Dynal, Oslo, Norway), microtiter well, plate, or column). Immobilization is accomplished either directly to the support or through a specific binding pair interaction with a substance which is itself immobilized on the support; examples of binding pairs which may be used for immobilization purposes include antigen/antibody pairs, DNA binding protein/DNA binding site pairs (for example, the GCN4 protein and its DNA binding site), enzyme/substrate pairs, lectin/carbohydrate pairs, base-paired or ligated nucleic acids, avidin/biotin, and protein A/immunoglobulin; in particular preferred examples, one skilled in the art may immobilize an Hmp-streptavidin fusion protein on a biotin-coated surface, an Hmp-protein A fusion protein on an immunoglobulin-coated surface (or the reverse of either) or may immobilize a cysteine-containing Hmp polypeptide derivative through disulfide bridges to a support or to another cysteine-containing protein bound to the support.

Once immobilized, the Hmp polypeptide is contacted with a test nucleic acid under conditions allowing formation of a complex between the Hmp polypeptide and a mismatch included in the nucleic acid sequence. If the sequence contains a mismatch (for example, due to a mutation in the test nucleic acid strand), the sequence is captured by the immobilized Hmp polypeptide and may be detected directly or indirectly by any standard technique, including detection of a labeled nucleic acid strand (for example, with a radioactive or fluorescent label) in association with the solid support, or by the use of a labeled nucleotide probe complementary, for example, to a portion of the captured control nucleic acid sequence.

As discussed above, this particular type of format facilitates the identification of a mismatch-containing nucleotide sequence, even when present in a background of a very large number of homoduplex molecules. If desired, the mismatch-containing sequence, once captured, may be amplified (for example, by PCR or LCR) to facilitate further analysis, such as fine mapping of the mismatch location by nucleic acid sequencing.

In an alternative detection format, the duplex (rather than the Hmp polypeptide) is immobilized on a solid support (as described above), and binding by Hmp polypeptide is detected. In this format, detection may also be accomplished by any standard method, for example, by detection of labeled Hmp polypeptide in association with the solid support or by detection of labeled Hmp polypeptide-specific antibodies (or secondary labeled antibodies). Again, any appropriate label may be utilized, for example, any radioactive or fluorescent marker may be used or, alternatively, any enzyme marker may be utilized, including (without limitation) alkaline phosphatase or horseradish peroxidase, and detection accomplished by addition of a chromogenic or fluorogenic substrate.

In yet another alternative assay format, Hmp polypeptide is reacted with and bound to a mismatch-containing sequence in solution, and the complex subsequently isolated or identified, for example, by filter binding, immunoprecipitation, or gel electrophoretic resolution. Again, the isolated complex may be detected by any of the methods described above.

If fluorescent labels are utilized in any of the above techniques, label detection may be automated using an automated fluorometer. In this system, detection is accomplished either by direct fluorescence measurement or by measurement of fluorescence polarization (that is, measurement of the change in the polarization-mediated spin of a molecule, for example, a duplex sequence, upon binding to another molecule, for example, an antibody or an Hmp polypeptide). Using such fluorometers, measurements may be carried out manually on pre-formed mismatch:Hmp polypeptide complexes having a fluorescent label bound directly or indirectly to either the nucleotide or polypeptide component; or these complexes may first be captured by the fluorometer, for example, by utilizing a fluorometer that includes microparticles bound to capture reagents (such as an Hmp polypeptide or an Hmp polypeptide-specific antibody). If desired, these systems may be used with test or control nucleic acids that have been previously amplified (for example, by PCR or LCR). Although any fluorescent label may be utilized, a preferred labeling system includes an alkaline phosphatase tag and a methyl umbelliferone phosphate substrate. Fluorometers are available from a number of commercial manufacturers and include the LCx and IMx systems available from Abbott Laboratories.

In one preferred approach using a fluorometer system, microparticles bound to Hmp polypeptides are used as capture reagents to isolate fluorescently labeled mismatch-containing sequences, and the sequences are then detected. Alternatively, Hmp polypeptides may be complexed with a mismatch-containing sequence, and the event detected as a change in the polarization-mediated spin, as compared to the nucleic acid sequence alone.

Other Embodiments

Polypeptides according to the invention include the entire Ustilago Hmp1 polypeptide (as shown in FIG. 2; SEQ ID NO: 2) as well as any analog or fragment of this polypeptide. Polypeptides of the invention also include all mRNA processing variants (e.g., all products of alternative splicing or differential promoter utilization) as well as analogous Hmp polypeptides from Ustilago or other organisms, including but not limited to fungi, plants, viruses, and animals.

Specific Hmp1 polypeptide fragments or analogues of interest include full-length or partial (see below) proteins including an amino acid sequence which differs only by conservative amino acid substitutions, for example, substitution of one amino acid for another of the same class (e.g., valine for glycine, arginine for lysine, etc.) or by one or more non-conservative amino acid substitutions, deletions, or insertions located at positions of the amino acid sequence which do not destroy its mismatch binding activity (as assayed above or according to any other standard method). Analogs also include Hmp polypeptides which are modified for the purpose of increasing peptide stability; such analogs may contain, e.g., one or more desaturated peptide bonds or D-amino acids in the peptide sequence, or the peptide may be formulated as a cyclized peptide molecule.

Hmp polypeptides may be used to detect a mismatch in any test nucleotide sequence, and any control nucleotide sequence may be utilized for comparison purposes. The test and/or control nucleic acids may be derived from any eukaryotic cell, eubacterial cell, bacteriophage, DNA virus, or RNA virus, including, without limitation, human T-cell leukemia virus, human immunodeficiency virus (for example, HTLV-I, HTLV-II, HIV-1, and HIV-2), any one of the family Adenoviridae, Papovaviridae, or Herpetoviridae, any member of the order Spirochaetales, Kinetoplastida, or Actinomycetales, of the family Treponemataceae, Trypoanosomatidae, or Mycobacteriaceae, and of the species *Mycobacterium tuberculosis, Treponema pallidum, Treponema pertenue, Borrelia burgdorferi*, or *Trypanosoma cruzi*.

Control nucleic acids may include an oncogene or a tumor suppressor gene of a eukaryotic (for example, mammalian) cell; preferable mammalian oncogenes include, without limitation, BRCA-1, BRCA-2, abl, akt, crk, erb-A, erb-B, ets, fes/fps, fgr, fms, fos, jun, kit, mil/raf, mos, myb, myc, H-ras, K-ras, rel, ros, sea, sis, ski, src, and yes; preferable tumor suppressor genes include p53, retinoblastoma (preferably RB1), adenomatous polyposis coli, NF-1, NF-2, MLH-1, MTS-1, MSH-2, and human non-polyposis genes.

Alternatively, a control nucleic acid may be isolated from any one of the β-globin, phenylalanine hydroxylase, $α_1$-antitrypsin, 21-hydroxylase, pyruvate dehydrogenase E1α-subunit, dihydropteridine reductase, rhodopsin, β-amyloid, nerve growth factor, superoxide dismutase, Huntington's disease, cystic fibrosis, adenosine deaminase, β-thalassemia, ornithine transcarbamylase, collagen, bcl-2, β-hexosaminidase, topoisomerase II, hypoxanthine phosphoribosyltransferase, phenylalanine 4-monooxygenase, Factor VIII, Factor IX, nucleoside phosphorylase, glucose-6-phosphate dehydrogenase, phosphoribosyltransferase, Duchenne muscular dystrophy, von Hippel Lindau, or the mouse modelled Menkes genes. Control nucleic acids may also be derived from any cell cycle control gene, preferably p21, p27, or p16.

The control and/or test nucleic acids may be any nucleotide-containing molecule including, without limitation, a restriction fragment, a sequence produced by amplification via PCR, LCR, RACE, NASBA, SDA, or any other preparative amplification method, or a sequence propagated in any prokaryotic or eukaryotic cell, bacteriophage, eubacterial cell, insect virus (e.g., using a baculovirus-derived vector), or animal virus (e.g., using an SV40- or adenovirus-derived vector).

Control and test nucleic acids may be DNA or RNA, and may include modified or derivatized bases. In addition, either or both of these nucleic acids may include unusual base linkages; for example, either or both nucleic acids may include peptide bonds (i.e., may be a peptide nucleic acid or PNA).

Individuals skilled in the art will readily recognize that the compositions of the present invention can be used in methods and/or assembled into kits for the detection of mismatches, e.g., mismatches diagnostic of human diseases. Such methods and kits find use in the areas of cancer diagnosis and prognosis, perinatal screening for inherited diseases, differential diagnosis of diseases not readily detectable by conventional tests (for example, Marfan's syndrome and the fragile X syndrome), and the analysis of genetic polymorphisms (for example, for genetic mapping, tissue matching, or identification purposes).

In addition, such methods and kits may be used to quantitate the number of mutations in a given test sample, simply by quantitating the amount of Hmp polypeptide bound to a test nucleotide sequence. This approach allows one skilled in the art to measure the total number of mutations in a gene therapy construct or to measure genetic variation at quantitative trait loci. Quantitation of mismatch-bound Hmp polypeptide may be accomplished by any standard technique, for example, using labeled Hmp polypeptide or labeled Hmp polypeptide-specific antibodies in the methods described above. If desired, sequences that include pre-determined numbers of mismatches may be included as controls in these assays.

Those skilled in the art will also recognize that the invention is useful for yet other purposes. For example, the claimed methods facilitate detection of single base pair mismatches in cloned DNA, for example, mutations introduced during experimental manipulations (e.g., transformation, mutagenesis, PCR amplification, or after prolonged storage or freeze:thaw cycles). This method is therefore particularly useful for testing genetic constructs that express therapeutic proteins or that are introduced into a patient for gene therapy purposes.

The methods may also be used for rapid typing of bacterial or viral strains. By "type" is meant to characterize an isogeneic bacterial or viral strain by detecting one or more nucleic acid mutations that distinguishes the particular strain from other strains of the same or related bacteria or virus. As an example, genetic variation of the human immunodeficiency virus has led to the isolation of distinct HIV types, each bearing distinguishing gene mutations (Lopez-Galindez et al., *Proc. Natl. Acad. Sci. USA* 88: 4280 (1991)). Other examples of test nucleic acids of particular interest for typing include those isolated from viruses of the family Retroviridae, for example, the human T-lymphocyte viruses or human immunodeficiency viruses (in particular any one of HTLV-I, HTLV-II, HIV-1, or HIV-2), DNA viruses of the family Adenoviridae, Papovaviridae, or Herpetoviridae, bacteria, or other organisms, for example, organisms of the order Spirochaetales, of the genus Treponema or Borrelia, of the order Kinetoplastida, of the species *Trypanosoma cruzi*, of the order Actinomycetales, of the family Mycobacteriaceae, of the species *Mycobacterium tuberculosis*, or of the genus Streptococcus.

Typically, the kits of the invention will include at least one recombinant or substantially pure Hmp polypeptide (e.g., recombinant Hmp1 or Hmp1 purified from *Ustilago maydis* or any other appropriate organism). The kit may also include pre-formed heteroduplexes with which to standardize reaction conditions and/or appropriate buffers (for example, enzyme dilution buffers or enzyme reaction buffers).

In addition, to carry out various detection methods described above, kits according to the invention may include an Hmp polypeptide directly or indirectly bound to a solid support (for example, a filter or bead, such as a magnetic bead), or the kit may include an Hmp-streptavidin, Hmp-biotin, Hmp-protein A, or Hmp-immunoglobulin fusion protein and a solid support (for example, a filter, bead, or magnetic bead, such as a Dynabead) to which is immobilized the specific binding partner appropriate for that Hmp fusion protein (for example, streptavidin for biotin and protein A for immunoglobulin).

All publications and patents mentioned in this specification are herein incorporated by reference to the same extent as if each individual publication or patent was specifically and individually indicated to be incorporated by reference.

Other embodiments are within the following claims.

SEQUENCE LISTING (1) GENERAL INFORMATION:

(iii) NUMBER OF SEQUENCES: 32

(2) INFORMATION FOR SEQ ID NO: 1:

(i) SEQUENCE CHARACTERISTICS:
      (A) LENGTH: 555
      (B) TYPE: Nucleic Acid
      (C) STRANDEDNESS: Single
      (D) TOPOLOGY: Linear (iv) ANTI-SENSE: NO (xi) SEQUENCE DESCRIPTION: SEQ ID NO: 1:

```
CAACCTCATC AAACACTAAT TCACAATGTC TGAGCCCTCC AAGGTTAACG          50

GGTATGTTTC TCGTCACCAC ACAACATGTT GATCTCTGCG CTGCCGTCAA         100

ACAGCTTTCT AACCACTGCA CCCTCTGCTC TATCCGCACA CAGAAACTAC         150

AACTCGGTCG CTGGTACCGT CAAGGAGACC ATCGGCAACG CTCTCGGCTC         200

CACTGAGTGG CAAAAGGCTG GCAAGGAGCA GCACGCCAAG GGCGAGGGCG         250

AGATCAAGGC TGCTCAGGCC CAGGGCTACG CCGAGGGCAC TAAGGACCAG         300

GTCTCGGGTA AGATCGACAA CGTTGTCGGC GCTGTCACCG GTGACAAGTC         350

CAAGGAACTG TCCGGCAAGG CTCAGCAGGA GTCTGGCAAG GCTCAGAAGG         400

AGATCAACTC CTAAACGGTT ATTTGTTCGA ATTGATTTGA TAGATCATCA         450

GTCAATCAGC TCTCTACCTT ACGCTTAATC GTACAACGTA GGCATGCCAA         500
```

TGAATATACC AATCCAGANT GTCACAATTC TCATGTTAAA AAAAAAAAAA        550

AAAAA                                                         555

(2) INFORMATION FOR SEQ ID NO: 2:

(i) SEQUENCE CHARACTERISTICS:
        (A) LENGTH: 98
        (B) TYPE: Amino Acid
        (D) TOPOLOGY: Linear (xi) SEQUENCE DESCRIPTION: SEQ ID NO: 2:

MET SER GLU PRO SER LYS VAL ASN GLY ASN TYR ASN SER VAL ALA
1               5                   10                  15

GLY THR VAL LYS GLU THR ILE GLY ASN ALA LEU GLY SER THR GLU
                20                  25                  30

TRP GLN LYS ALA GLY LYS GLU GLN HIS ALA LYS GLY GLU GLY GLU
                35                  40                  45

ILE LYS ALA ALA GLN ALA GLN GLY TYR ALA GLU GLY THR LYS ASP
                50                  55                  60

GLN VAL SER GLY LYS ILE ASP ASN VAL VAL GLY ALA VAL THR GLY
                65                  70                  75

ASP LYS SER LYS GLU LEU SER GLY LYS ALA GLN GLN GLU SER GLY
                80                  85                  90

LYS ALA GLN LYS GLU ILE ASN SER
                95

(2) INFORMATION FOR SEQ ID NO: 3:

(i) SEQUENCE CHARACTERISTICS:
        (A) LENGTH: 386
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 3:

ATGTCTGAGC CCTCCAAGGT TAACGGGTAT GTTTCTCGTC ACCACACAAC          50

ATGTTGATCT CTGCGCTGCC GTCAAACAGC TTTCTAACCA CTGCACCCTC         100

TGCTCTATCC GCACACAGAA ACTACAACTC GGTCGCTGGT ACCGTCAAGG         150

AGACCATCGG CAACGCTCTC GGCTCCACTG AGTGGCAAAA GGCTGGCAAG         200

GAGCAGCACG CCAAGGGCGA GGGCGAGATC AAGGCTGCTC AGGCCCAGGG         250

CTACGCCGAG GGCACTAAGG ACCAGGTCTC GGGTAAGATC GACAACGTTG         300

TCGGCGCTGT CACCGGTGAC AAGTCCAAGG AACTGTCCGG CAAGGCTCAG         350

CAGGAGTCTG GCAAGGCTCA GAAGGAGATC AACTCC                       386

(2) INFORMATION FOR SEQ ID NO: 4:

(i) SEQUENCE CHARACTERISTICS:
        (A) LENGTH: 14
        (B) TYPE: Amino Acid
        (D) TOPOLOGY: Linear (xi) SEQUENCE DESCRIPTION: SEQ ID NO: 4:

GLU THR ILE GLY ASN ALA LEU GLY SER THR GLU TRP GLN LYS
1               5                   10

(2) INFORMATION FOR SEQ ID NO: 5:

(i) SEQUENCE CHARACTERISTICS:
        (A) LENGTH: 27
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 5:

ACGGATCCGC NCAAGGCNCA AGGGNTA                                  27

(2) INFORMATION FOR SEQ ID NO: 6:

(i) SEQUENCE CHARACTERISTICS:
        (A) LENGTH: 31
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 6:

CGGAATTCTT AGTCNATTCT TNCCNNTANA C                              31

(2) INFORMATION FOR SEQ ID NO: 7:

(i) SEQUENCE CHARACTERISTICS:
        (A) LENGTH: 30
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 7:

GCGGATCCCA AGGAGTCACA ATGTCTGAGC                                30

(2) INFORMATION FOR SEQ ID NO: 8:

(i) SEQUENCE CHARACTERISTICS:
        (A) LENGTH: 21
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 8:

GCGGATCCGT TTAGGAGTTG A                                            21

(2) INFORMATION FOR SEQ ID NO: 9:

(i) SEQUENCE CHARACTERISTICS:
        (A) LENGTH: 62
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 9:

GTCTAAGCTT AGCTGAATTC GTCTCCGTGT TCACGGAGA CGAATTTCGA          50

TGAGGATCCA TC                                                            62

(2) INFORMATION FOR SEQ ID NO: 10:

(i) SEQUENCE CHARACTERISTICS:
            (A) LENGTH: 61
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 10:

TGATGGATCC TCATCGAATT CGTAGGATGC TTTGCATCCT ACGAATTCAG                50

CTAAGCTTAG A                                                         61

(2) INFORMATION FOR SEQ ID NO: 11:

(i) SEQUENCE CHARACTERISTICS:
            (A) LENGTH: 61
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 11:

TGATGGATCC TCATCGAATT CGTCTCCGTG AAACACGGAG ACGAATTCAG                50

CTAAGCTTAG A                                                         61

(2) INFORMATION FOR SEQ ID NO: 12:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 12:

GCAGTGTCCA CCAGTCTTGT CCTGGTCTCC ATACCTTGAT GTACGGATCT                50

(2) INFORMATION FOR SEQ ID NO: 13:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 13:

GCAGTGTCCA CCAGTCTTGT CCTGCTCTCC ATACCTTGAT GTACGGATCT                50

(2) INFORMATION FOR SEQ ID NO: 14:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 14:

GCAGTGTCCA CCAGTCTTGT CCTGTTCTCC ATACCTTGAT GTACGGATCT                50

(2) INFORMATION FOR SEQ ID NO: 15:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 15:

GCAGTGTCCA CCAGTCTTGT CCTGATCTCC ATACCTTGAT GTACGGATCT                50

(2) INFORMATION FOR SEQ ID NO: 16:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 16:

AGATCCGTAC ATCAAGGTAT GGAGACCAGG ACAAGACTGG TGGACACTGC                50

(2) INFORMATION FOR SEQ ID NO: 17:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 17:

AGATCCGTAC ATCAAGGTAT GGAGATCAGG ACAAGACTGG TGGACACTGC                50

(2) INFORMATION FOR SEQ ID NO: 18:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 18:

AGATCCGTAC ATCAAGGTAT GGAGAACAGG ACAAGACTGG TGGACACTGC                50

(2) INFORMATION FOR SEQ ID NO: 19:

(i) SEQUENCE CHARACTERISTICS:
            (A) LENGTH: 50
            (B) TYPE: Nucleic Acid
            (C) STRANDEDNESS: Single
            (D) TOPOLOGY: Linear (iv) ANTI-SENSE: NO (xi) SEQUENCE DESCRIPTION: SEQ ID NO: 19:

AGATCCGTAC ATCAAGGTAT GGAGAGCAGG ACAAGACTGG TGGACACTGC                50

(2) INFORMATION FOR SEQ ID NO: 20:

(i) SEQUENCE CHARACTERISTICS:
            (A) LENGTH: 34
            (B) TYPE: Nucleic Acid
            (C) STRANDEDNESS: Single (D) TOPOLOGY: Linear (iv) ANTI-SENSE: NO (xi) SEQUENCE DESCRIPTION: SEQ ID NO: 20:

ACAGAATTCT CGGCACTTTG TGCCGAGAAT TCTG                              34

(2) INFORMATION FOR SEQ ID NO: 21:

(i) SEQUENCE CHARACTERISTICS:
        (A) LENGTH: 34
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 21:

ACAGAATTCT CGGCACTTTC TGCCGATAAT TCTG                              34

(2) INFORMATION FOR SEQ ID NO: 22:

(i) SEQUENCE CHARACTERISTICS:
        (A) LENGTH: 34
        (B) TYPE: Nucleic Acid
        (C) STRANDEDNESS: Single
        (D) TOPOLOGY: Linear (iv) ANTI-SENSE: NO (xi) SEQUENCE DESCRIPTION: SEQ ID NO: 22:

ACAGAATTCT CGGCACTTTG TGCCGCTAAT TCTG                              34

(2) INFORMATION FOR SEQ ID NO: 23:

(i) SEQUENCE CHARACTERISTICS:
        (A) LENGTH: 22
        (B) TYPE: Amino Acid
        (D) TOPOLOGY: Linear (xi) SEQUENCE DESCRIPTION: SEQ ID NO: 23:

ALA ALA ALA GLN ALA GLN GLY TYR ALA GLU GLY THR LYS ASP GLN
1               5                  10                  15
VAL SER GLY LYS ILE ASP ASN
            20

(2) INFORMATION FOR SEQ ID NO: 24:

(i) SEQUENCE CHARACTERISTICS:
        (A) LENGTH: 10
        (B) TYPE: Amino Acid
        (D) TOPOLOGY: Linear (xi) SEQUENCE DESCRIPTION: SEQ ID NO: 24:

MET SER GLU PRO SER LYS VAL ASN GLY ASN
1               5                  10

(2) INFORMATION FOR SEQ ID NO: 25:

(i) SEQUENCE CHARACTERISTICS:
        (A) LENGTH: 4
        (B) TYPE: Amino Acid
        (D) TOPOLOGY: Linear (xi) SEQUENCE DESCRIPTION: SEQ ID NO: 25:

TYR ASN SER VAL
1

(2) INFORMATION FOR SEQ ID NO: 26:

(i) SEQUENCE CHARACTERISTICS:
        (A) LENGTH: 28
        (B) TYPE: Amino Acid
        (D) TOPOLOGY: Linear (xi) SEQUENCE DESCRIPTION: SEQ ID NO: 26:

```
ALA GLY THR VAL LYS GLU THR ILE GLY ASN ALA LEU GLY SER THR
1               5                  10                  15
GLU TRP GLN LYS ALA GLY LYS GLU GLN HIS ALA LYS GLY
20                  25
```

(2) INFORMATION FOR SEQ ID NO: 27:

(i) SEQUENCE CHARACTERISTICS:
        (A) LENGTH: 8
        (B) TYPE: Amino Acid
        (D) TOPOLOGY: Linear (xi) SEQUENCE DESCRIPTION: SEQ ID NO: 27:

```
GLU GLY GLU ILE LYS ALA ALA GLN
1               5
```

(2) INFORMATION FOR SEQ ID NO: 28:

(i) SEQUENCE CHARACTERISTICS:
        (A) LENGTH: 32
        (B) TYPE: Amino Acid
        (D) TOPOLOGY: Linear (xi) SEQUENCE DESCRIPTION: SEQ ID NO: 28:

```
PHE GLY ASN PRO GLU THR THR THR GLY GLY ASN ALA LEU LYS PHE
1               5                  10                  15
TYR ALA SER VAL ARG LEU ASP ILE ARG ARG ILE GLY ALA VAL LYS
                20                  25                  30
GLU GLY
```

(2) INFORMATION FOR SEQ ID NO: 29:

(i) SEQUENCE CHARACTERISTICS:
        (A) LENGTH: 33
        (B) TYPE: Amino Acid
        (D) TOPOLOGY: Linear (xi) SEQUENCE DESCRIPTION: SEQ ID NO: 29:

```
GLU ASN VAL VAL GLY SER GLU THR ARG VAL LYS VAL VAL LYS ASN
1               5                  10                  15
LYS ILE ALA ALA PRO PHE LYS GLN ALA GLU PHE GLN ILE LEU TYR
                20                  25                  30
ALA GLN GLY
```

(2) INFORMATION FOR SEQ ID NO: 30:

(i) SEQUENCE CHARACTERISTICS:
        (A) LENGTH: 29
        (B) TYPE: Amino Acid
        (D) TOPOLOGY: Linear (xi) SEQUENCE DESCRIPTION: SEQ ID NO: 30:

```
TYR ALA GLU GLY THR LYS ASP GLN VAL SER GLY LYS ILE ASP ASN
1               5                  10                  15
```

-continued

```
VAL VAL GLY ALA VAL THR GLY ASP LYS SER LYS GLU LEU SER
                20                  25

(2) INFORMATION FOR SEQ ID NO: 31:

(i) SEQUENCE CHARACTERISTICS:
        (A) LENGTH:  4
        (B) TYPE:  Amino Acid
        (D) TOPOLOGY:  Linear (xi) SEQUENCE DESCRIPTION:  SEQ ID NO: 31:

GLY LYS ALA GLN
1

(2) INFORMATION FOR SEQ ID NO: 32:

(i) SEQUENCE CHARACTERISTICS:
        (A) LENGTH:  69
        (B) TYPE:  Amino Acid
        (D) TOPOLOGY:  Linear (xi) SEQUENCE DESCRIPTION:  SEQ ID NO: 32:

GLN GLU SER GLY LYS ALA GLN LYS GLU ILE ASN SER GLY GLU GLY
1               5                   10                  15

ILE ASN PHE TYR GLY GLU LEU VAL ASP LEU GLY VAL LYS GLU LYS
                20                  25                  30

LEU ILE GLU LYS ALA GLY ALA TRP TYR SER TYR LYS GLY GLU LYS
                35                  40                  45

ILE GLY GLN GLY LYS ALA ASN ALA THR ALA TRP LEU LYS ASP ASN
                50                  55                  60

PRO GLU THR ALA LYS GLU ILE GLU LYS
                65
```

What is claimed is:

1. An isolated polynucleotide sequence consisting of nucleotides 1 to 386 set forth in SEQ ID NO:3.

2. The isolated polynucleotide segment of claim 1, wherein the isolated polynucleotide is DNA and RNA.

3. A vector comprising the isolated polynucleotide segment of claim 1.

4. A host cell transformed with the vector of claim 3 to express the isolated polynucleotide segment.

5. A process for producing a polypeptide of the isolated polynucleotide comprising the steps of culturing the host cell of claim 4 under conditions sufficient for the production of said polypeptide, which is encoded by the isolated polynucleotide segment.

6. An isolated recombinant helix modification recognition protein polypeptide encoded by a polynucleotide sequence consisting of SEQ ID NO:3 fused to bacteriophage T4 endonuclease VII.

7. An isolated polynucleotide segment comprising a first polynucleotide sequence, wherein the first polynucleotide sequence encodes a polypeptide sequence selected from the group consisting of:
   (a) a first sequence comprising the amino acid sequence of SEQ ID NO:2;
   (b) a second sequence comprising a portion of the amino acid sequence of SEQ ID NO:2;
       wherein the polypeptide sequence generates antibodies having binding specificity for the amino acid sequence set forth in SEQ ID NO:2.

8. The isolated polynucleotide segment of claim 7, wherein the isolated polynucleotide segment is DNA or RNA.

9. A vector comprising the isolated polynucleotide segment of claim 7.

10. A host cell transformed with the vector of claim 9.

11. A process for producing a polypeptide of the first polynucleotide sequence comprising the steps of culturing the host cell of claim 10 under conditions sufficient for the production of said polypeptide, which is encoded by the first polynucleotide segment.

12. The isolated polynucleotide segment of claim 7, wherein the first polynucleotide sequence encodes a polypeptide sequence consisting of the first sequence.

13. A vector comprising the isolated polynucleotide segment of claim 12.

14. A host cell transformed with the vector of claim 13.

15. A process for producing a polypeptide of the first polynucleotide sequence comprising the step of culturing the host cell of claim 14 under conditions sufficient for the production of said polypeptide, which is encoded by the first polynucleotide segment.

16. An isolated polynucleotide segment, comprising a first polynucleotide sequence, wherein the first polynucleotide sequence is selected from the group consisting of:
   (a) a first sequence having nucleotides 1 to 555 of SEQ ID NO:1;
   (b) a second sequence having nucelotides 1 to 414 of SEQ ID NO:1; and
   (c) a third sequence having nucleotides 1 to 386 of SEQ ID NO:1.

17. An isolated polynucleotide segment comprising a nucleotide sequence which is fully complementary to the polynucleotide segment of claim 16.

18. The isolated polynucleotide segment of claim 16, wherein the isolated polynucleoide segment is DNA o RNA.

19. A vector comprising the isolated polynucleotide segment of claim 16.

20. A host cell transformed with the vector of claim 19.

21. A process for producing a polypeptide of the first polynucleotide sequence comprising the steps of culturing the host cell of claim 20 under conditions sufficient for the production of said polypeptide, which is encoded by the first polynucleotide segment.

22. A recombinant polynucleotide segment, comprising a polynucleotide sequence, wherein the polynucleotide sequence (a) is SEQ ID NO:1, or (b) is the full complement of the entire length of SEQ ID NO: 1.

23. A vector comprising the recombinant polynucleotide segment of claim 22.

24. A host cell transformed with the vector claim 23.

25. A recombinant polynucleotide segment, comprising a polynucleotide sequence, wherein the polynucleotide sequence is (a) nucleotides 1 to 414 of SEQ ID NO:1, or (b) the full complement of the entire length of (a).

26. A vector comprising the recombinant polynucleotide segment of claim 25.

27. A host cell transformed with the vector of claim 26.

28. A recombinant polynucleotide segment, comprising a polynucleotide sequence, wherein the polynucleotide sequence (a) encodes a polypeptide comprising the amino acid sequence of SEQ ID NO:2, or (b) is the full complement of the entire length of a reference sequence that encodes a polypeptide comprising the amino acid sequence of SEQ ID NO:2.

29. A vector comprising the recombinant polynucleotide segment of claim 28.

30. The vector of claim 29, wherein the recombinant polynucleotide segment encodes the polypeptide.

31. A host cell transformed with the vector of claim 29.

32. A host cell transformed with the polynucleotide segment of claim 28 to express the polynucleotide sequence.

33. A process for producing the polypeptide comprising the steps of culturing the host cell of claim 32 under conditions sufficient for the production of the polypeptide, which is encoded by the first polynucleotide segment.

34. An isolated polynucleotide segment comprising a first polynucleotide or the complement of the entire length of said first polynucleotide, which first polynucleotide encodes a reference polypeptide wherein the reference polypeptide is (a) the amino acid sequence of SEQ ID NO:2, or (b) is identical to the amino acid sequence of SEQ ID NO:2 except that, over the entire length corresponding to the amino acid sequence of SEQ ID NO:2, the reference polypeptide has a substitution, deletion or insertion of one amino acid.

35. A vector comprising the polynucleotide of claim 34.

36. A host cell transformed with the vector of claim 35.

37. A process for producing helix modification recognition protein polypeptide comprising the step of culturing the host cell of claim 36 under conditions sufficient for the production of said polypeptide, where said polypeptide (a) is the amino acid sequence of SEQ ID NO:2 or (b) is identical to the amino acid sequence of SEQ ID NO:2, except that, over the entire length corresponding to the amino acid sequence of SEQ ID NO:2, the polypeptide has a substitution, deletion or insertion of one amino acid.

38. A polynucleotide encoding a fusion polypeptide having a segment having the amino acid sequence set forth in SEQ ID NO:2, or an amino acid sequence which is identical with SEQ ID NO:2 except that, over the entire length corresponding to SEQ ID NO:2, the amino acid sequence has a substitution, insertion or deletion of one amino acid.

39. An isolated polynucleotide segment comprising a DNA sequence or an RNA sequence encoding the amino acid sequence set forth in SEQ ID NO:2, obtained by screening a sample of a nucleic acid library, under stringent hybridization conditions with a probe having a polynucleotide sequence encoding the amino acid sequence set forth in SEQ ID NO:2 or a fragment thereof, which fragment retains binding activity to mismatched nucleotide bases; and isolating said DNA sequence or RNA sequence.

40. An isolated polynucleotide segment comprising a first polynucleotide sequence encoding a polypeptide having the amino acid sequence set forth in SEQ ID NO:2, or a fragment thereof, which fragment retains binding activity to mismatched nucleotide bases, wherein the first polynucleotide sequence is obtained by amplifying a sample of a nucleic acid library, under amplification conditions with a pair of primers having sequences as set forth in SEQ ID NO:5 and SEQ ID NO:6; and isolating said polynucleotide sequence.

41. The isolated polynucleotide segment of claim 40, wherein the pair of primers have sequences are as set forth in SEQ ID NO:7 and SEQ ID NO:8.

42. An isolated recombinant helix modification recognition protein polypeptide having the amino acid sequence of SEQ ID NO: 2.

43. The isolated recombinant helix modification recognition protein polypeptide of claim 42, wherein the polypeptide has the amino acid sequence identical to the amino acid sequence of SEQ ID NO: 2 except that, over the entire length corresponding to the amino acid sequence of SEQ ID NO:2, the isolated polypeptide has a substitution, deletion or insertion of one amino acid.

* * * * *

UNITED STATES PATENT AND TRADEMARK OFFICE
CERTIFICATE OF CORRECTION

PATENT NO. : 6,232,095 B1
DATED : May 15, 2001
INVENTOR(S) : Kmiec et al.

It is certified that error appears in the above-identified patent and that said Letters Patent is hereby corrected as shown below:

<u>Title page,</u>
Item [73], please insert the following Assignee after "Thomas Jefferson University, Philadelphia, PA (US)"
-- Cornell Research Foundation, Inc., Ithaca, NY (US) --

Signed and Sealed this

Tenth Day of June, 2003

JAMES E. ROGAN
*Director of the United States Patent and Trademark Office*